(12) United States Patent
Christ et al.

(10) Patent No.: US 8,026,365 B2
(45) Date of Patent: Sep. 27, 2011

(54) 4,4-DISUBSTITUTED PIPERIDINE DERIVATIVES

(75) Inventors: Andreas Christ, Arleshiem (CH); Rainer Martin, Basel (CH); Peter Mohr, Basel (CH)

(73) Assignee: Hoffman-La Roche Inc., Nutley, NJ (US)

( * ) Notice: Subject to any disclaimer, the term of this patent is extended or adjusted under 35 U.S.C. 154(b) by 755 days.

(21) Appl. No.: 12/111,230

(22) Filed: Apr. 29, 2008

(65) Prior Publication Data

US 2008/0293756 A1    Nov. 27, 2008

(30) Foreign Application Priority Data

May 25, 2007  (EP) ..................................... 07108907

(51) Int. Cl.
*A61K 31/438* (2006.01)
*C07D 471/10* (2006.01)

(52) U.S. Cl. .............................. 546/16; 546/20; 514/278
(58) Field of Classification Search .......................... None
See application file for complete search history.

(56) References Cited

FOREIGN PATENT DOCUMENTS

| EP | 1619193 | 1/2006 |
|---|---|---|
| WO | WO 01/32633 | 5/2001 |
| WO | WO02/100849 | 12/2002 |
| WO | WO 03/037271 | 5/2003 |
| WO | WO 03/104236 A1 | 12/2003 |
| WO | WO 2004/000806 A1 | 12/2003 |
| WO | WO 2005/047249 | 5/2005 |
| WO | WO 2006/128803 | 12/2006 |

OTHER PUBLICATIONS

K. Cejvan, D. H. Coy and S. Efendic *Diabetes* 2003, 52, 1176-1181; M. Z. Strowski, R.
M. Parmar, A. D. Blake and J. M. Schaeffer *Endocrinology* 2000, 141, 111-117.
K. H. Bleicher, Y. Wüthrich, M. De Boni, S. Kolczewski, T. Hoffmann, A. J. Sleight *Bioorg. Med. Chem. Lett.* 2002, 12, 2519-2522.
I. Kompis and A. Wick *Helv. Chim. Acta* 1977, 60, 3025-3034.
S. P. Dudek, H. D. Sikes and C. E. D. Chidsey *J. Am. Chem. Soc.* 2001, 123, 8033-8038.
M. J. Ashton, D. C. Cook, G. Fenton, J.-A. Karlsson, M. N. Palfreyman, D. Raeburn, A. J. Ratcliffe, J. E. Souness, S. Thurairatnam and N. Vicker *J. Med. Chem.* 1994, 37, 1696-1703.
A. W. White, R. Almassy, A. H. Calvert, N. J. Curtin, R. J. Griffin, Z. Hostomsky, K. Maegley, D. R. Newell, S. Srinivasan and B. T. Golding *J. Med. Chem.* 2000, 43, 4084-4097.

*Primary Examiner* — Janet Andres
*Assistant Examiner* — Timothy R Rozof
(74) *Attorney, Agent, or Firm* — George W. Johnston; Dennis P. Tramaloni; Samuel H. Megerditchian

(57) ABSTRACT

This invention relates to 4,4-disubstituted piperidine derivatives of the formula

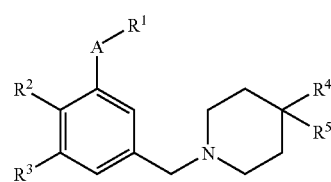

wherein A and $R^1$ to $R^5$ are as defined in the specification, and pharmaceutically acceptable salts thereof. The invention further relates to pharmaceutical compositions containing such compounds, to a process for their preparation and to their use for the treatment and/or prevention of diseases which are associated with the modulation of SST receptors subtype 5.

13 Claims, No Drawings

4,4-DISUBSTITUTED PIPERIDINE DERIVATIVES

PRIORITY TO RELATED APPLICATION(S)

This application claims the benefit of European Patent Application No. 07108907.2, filed May 25, 2007, which is hereby incorporated by reference in its entirety.

FIELD OF THE INVENTION

The present invention is concerned with compounds of the general formula I

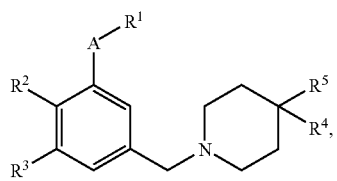

and pharmaceutically acceptable salts thereof.

The compounds of formula I possess pharmaceutical activity, in particular they are modulators of somatostatine receptor activity. More particularly, the compounds are antagonists of the somatostatine receptor subtype 5 (SSTR5).

All documents cited below are expressly incorporated herein by reference.

BACKGROUND

Diabetes mellitus is a systemic disease characterized by metabolic disorders involving insulin, carbohydrates, fats and proteins, and disorders in the structure and function of blood vessels. The primary symptom of acute diabetes is hyperglycemia, often accompanied by glucosuria, the presence in urine of large amounts of glucose, and polyuria, the excretion of large volumes of urine. Additional symptoms arise in chronic diabetes, including degeneration of the walls of blood vessels. Although many different human organs are affected by these vascular changes, the eyes and kidneys appear to be the most susceptible. As such, long-standing diabetes mellitus, even when treated with insulin, is a leading cause of blindness.

There are three recognized types of diabetes mellitus. Type I diabetes or insulin dependent diabetes mellitus (IDDM) is typically of juvenile onset; ketosis develops early in life with much more severe symptoms and has a near-certain prospect of later vascular involvement. Control of Type I diabetes is difficult and requires exogenous insulin administration. Type II diabetes or non-insulin dependent diabetes mellitus (NIDDM) is ketosis-resistant, generally develops later in life, is milder and has a more gradual onset. Gestational diabetes is related to Type II diabetes and associated with an increased risk of later development of that disease. Type III diabetes is malnutrition-related diabetes.

NIDDM is a condition that poses a major threat to the health of the citizens of the western world. NIDDM accounts for over 85% of diabetes incidence worldwide and about 160 million people are suffering from NIDDM. The incidence is expected to increase considerably within the next decades, especially in developing countries. NIDDM is associated with morbidity and premature mortality resulting from serious complications, e.g., cardiovascular disease. NIDDM is characterized by both fasting and post-prandial hyperglycemia resulting from abnormalities in insulin secretion and insulin action.

The hyperglycemia in patients suffering from NIDDM can usually be initially treated by dieting, but eventually most NIDDM patients have to take oral antidiabetic agents and/or insulin injections to normalize their blood glucose levels. The introduction of orally effective hypoglycemic agents was an important development in the treatment of hyperglycemia by lowering blood glucose levels. These existing oral therapies which comprise a wide variety of biguanide, sulfonylurea and thiazolidinedione derivatives have been used clinically as hypoglycemic agents. However, all three classes of compound have side effects. The biguanides, for example metformin, are unspecific and in certain cases have been associated with lactic acidosis, and need to be given over a longer period of time, i.e. they are not suitable for acute administration. The sulfonylureas, though having good hypoglycemic activity, require great care during use because they frequently cause serious hypoglycemia and are most effective over a period of circa ten years. The thiazolidinediones may cause weight gain and deterioration of cardiovascular function following chronic administration and troglitazone has been associated with the occurrence of serious hepatic dysfunction.

Thus, there is a significant and rising need for antidiabetic drugs that have novel mechanisms of action, thereby avoiding side effects produced by known therapies. The hormone somatostatin (SST) is primarily produced in the intestinal tract and in the pancreas. In addition it acts as a neurotransmitter. The hormone is involved through its receptors in the regulation of several other hormones and in immunoregulation. In particular, SST suppresses the secretion of insulin by pancreatic β cells and the secretion of glucagon-like peptide 1 (GLP-1) by L cells.

Consequently, antagonizing the effect of SST would lead to increased peripheral glucose disposal and higher plasma insulin concentrations. Additionally, SSTR5 knockout mice demonstrated higher insulin sensitivity than littermates. In patients suffering from impaired glucose tolerance and NIDDM, these combined effects would moderate the dangerous hyperglycemia and accordingly reduce the risk of tissue damage. If such SSTR5 antagonists are sufficiently selective over the other four SST receptors, little influence is expected on secretion of other hormones. Particularly, selectivity over SST receptor subtype 2 avoids influences on glucagon secretion (K. Cejvan, D. H. Coy and S. Efendic *Diabetes* 2003, 52, 1176-1181; M. Z. Strowski, R. M. Parmar, A. D. Blake and J. M. Schaeffer *Endocrinology* 2000, 141, 111-117). Advantageous over established therapies is the dual mechanism of action to increase insulin secretion (directly on pancreatic β cells and indirectly through GLP-1 release from L cells) and to increase glucose disposal, whereby SSTR5 antagonists could have the potential to beneficially influence insulin resistance in patients with NIDDM. In summary, SSTR5 antagonists are expected to beneficially influence NIDDM, the underlying impaired fasting glucose and impaired glucose tolerance, as well as complications of long-standing, insufficiently controlled diabetes mellitus.

SUMMARY OF THE INVENTION

In an embodiment of the present invention, provided is a compound of formula I:

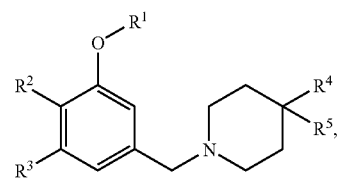

wherein
R¹ is selected from the group consisting of $C_{2-7}$-alkyl, $C_{2-7}$-alkenyl, $C_{3-7}$-alkinyl, $C_{3-7}$-cycloalkyl, halogen-$C_{1-7}$-alkyl, $C_{1-7}$-alkoxy-$C_{1-7}$-alkyl and benzyl;
R² is selected from the group consisting of hydrogen, $C_{1-7}$-alkyl,
  hydroxy, $C_{1-7}$-alkoxy, $C_{2-7}$-alkenyloxy,
  hydroxy-$C_{1-7}$-alkoxy, $C_{1-7}$-alkoxy-$C_{1-7}$-alkoxy,
  —O-benzyl, —O—$C_{3-7}$-cycloalkyl,
  halogen, halogen-$C_{1-7}$-alkyl, halogen-$C_{1-7}$-alkoxy,
  amino, pyrrolyl, imidazolyl,
  —C(O)OR⁶, wherein R⁶ is $C_{1-7}$-alkyl, and
  unsubstituted phenyl or phenyl substituted by one to three groups independently selected from $C_{1-7}$-alkyl, halogen and $C_{1-7}$-alkoxy;
R³ is hydrogen or $C_{1-7}$-alkoxy;
R⁴ is —NH—CO—R⁷, wherein R⁷ is a ring selected from phenyl or pyridyl, said ring being unsubstituted or substituted by one or two groups selected from $C_{1-7}$-alkyl or halogen;
R⁵ is —CO—NH₂ or —CN;
or R⁴ and R⁵ are bonded to each other to form a ring together with the carbon atom to which they are attached, and R⁴ and R⁵ together are:
  —NH—C(O)—NH—C(O)—,
  —C(O)—NR⁸—CH₂—CH₂—, wherein R⁸ is phenyl, or
  —N═CR⁹—NH—C(O)—, wherein R⁹ is phenyl;
and pharmaceutically acceptable salts thereof.

In another embodiment of the present invention, provided is a process for the manufacture of compounds according to formula I, comprising the steps of:
a) reacting a piperidine of the formula

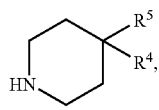
II wherein R⁴ and R⁵ are as defined above,
with an aldehyde of the formula

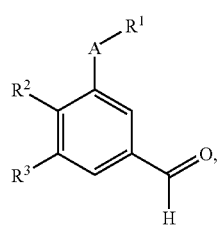
III wherein A and R¹ to R³ are as above,
by employing a reducing agent to obtain a compound of the formula

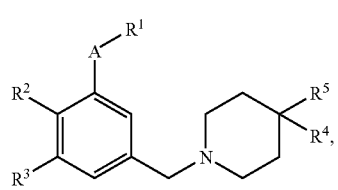
I and, if desired, converting the compound of formula I into a pharmaceutically acceptable salt; or, alternatively, b) alkylating a piperidine of the formula

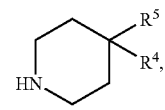
II wherein R⁴ and R⁵ are as defined above,
with a compound of the formula

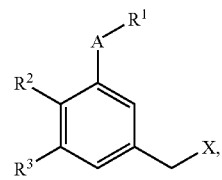
IV wherein A and R¹ to R³ are as defined above and X is a leaving group,
under basic conditions to obtain a compound of formula

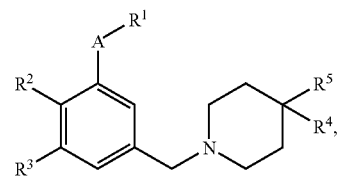
I and, if desired, converting the compound of formula I into a pharmaceutically acceptable salt; or, alternatively,
c) reacting a compound of the general formula

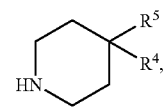
II wherein R⁴ and R⁵ are as defined above,
with a compound of the formula

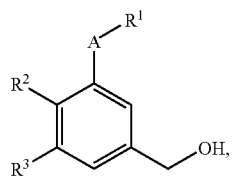
V wherein A and R¹ to R³ are as defined above, in the presence of a trialkylphosphine and a diazo-compound to obtain a compound of the formula

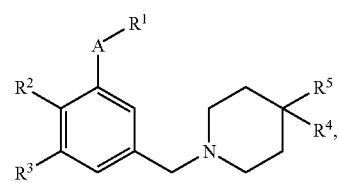
I and, if desired, converting the compound of formula I into a pharmaceutically acceptable salt.

In a further embodiment of the present invention, provided is a pharmaceutical composition, comprising a therapeutically effective amount of a compound according to formula I or a pharmaceutically acceptable salt thereof and a pharmaceutically acceptable carrier and/or adjuvent.

DETAILED DESCRIPTION

The present invention provides for selective, directly acting SSTR5 antagonists. Such antagonists are useful as therapeutically active substances, particularly in the treatment and/or prevention of diseases which are associated with the modulation of SST receptors subtype 5.

In the present description the term "alkyl", alone or in combination with other groups, refers to a branched or straight-chain monovalent saturated aliphatic hydrocarbon radical of one to twenty carbon atoms, preferably one to sixteen carbon atoms, more preferably one to ten carbon atoms.

The term "lower alkyl" or "$C_{1-7}$-alkyl", alone or in combination, signifies a straight-chain or branched-chain alkyl group with 1 to 7 carbon atoms, preferably a straight or branched-chain alkyl group with 1 to 4 carbon atoms. Examples of straight-chain and branched $C_1$-$C_7$ alkyl groups are methyl, ethyl, propyl, isopropyl, butyl, isobutyl, tert-butyl, the isomeric pentyls, the isomeric hexyls and the isomeric heptyls, preferably methyl, ethyl and isopropyl, and most preferred the groups specifically exemplified herein.

The term "lower alkenyl" or "$C_{2-7}$-alkenyl", alone or in combination, signifies a straight-chain or branched hydrocarbon residue comprising an olefinic bond and 2 to 7, preferably 2 to 6, particularly preferred 2 to 4 carbon atoms. Examples of alkenyl groups are ethenyl, 1-propenyl, 2-propenyl, isopropenyl, 1-butenyl, 2-butenyl, 3-butenyl and isobutenyl. A preferred example is 2-propenyl(allyl).

The term "lower alkinyl" or "$C_{3-7}$-alkinyl" signifies a straight-chain or branched hydrocarbon residue comprising a triple bond and 3 to 7, preferably 3 to 6, particularly preferred 3 to 4 carbon atoms. Examples of alkinyl groups are 2-propinyl, 2-butinyl and 3-butinyl. A preferred example is 2-propinyl.

The term "cycloalkyl" or "$C_{3-7}$-cycloalkyl" refers to a monovalent carbocyclic radical of three to seven, preferably three to five carbon atoms. This term is further exemplified by radicals such as cyclopropyl, cyclobutyl, cyclopentyl, cyclohexyl and cycloheptyl, with cyclopentyl being especially preferred.

The term "alkoxy" refers to the group R'—O—, wherein R' is alkyl. The term "lower alkoxy" or "$C_{1-7}$-alkoxy" refers to the group R'—O—, wherein R' is lower alkyl and the term "lower alkyl" has the previously given significance. Examples of lower alkoxy groups are e.g., methoxy, ethoxy, n-propoxy, isopropoxy, n-butoxy, iso-butoxy, sec-butoxy and tert-butoxy, preferably methoxy and ethoxy and most preferred the groups specifically exemplified herein.

The term "lower alkoxyalkyl" or "$C_{1-7}$-alkoxy-$C_{1-7}$-alkyl" refers to lower alkyl groups as defined above wherein at least one of the hydrogen atoms of the lower alkyl group is replaced by an alkoxy group as defined above. Among the preferred lower alkoxyalkyl groups are methoxymethyl, methoxyethyl and ethoxymethyl.

The term "lower alkoxyalkoxy" or "$C_{1-7}$-alkoxy-$C_{1-7}$-alkoxy" refers to lower alkoxy groups as defined above wherein at least one of the hydrogen atoms of the lower alkoxy group is replaced by an alkoxy group as defined above. Among the preferred lower alkoxyalkoxy groups are 2-methoxy-ethoxy and 3-methoxy-propoxy.

The term "halogen" refers to fluorine, chlorine, bromine and iodine, with fluorine, chlorine and bromine being preferred, and chlorine and bromine being most preferred.

The term "lower halogenalkyl" or "halogen-$C_{1-7}$-alkyl" refers to lower alkyl groups as defined above wherein at least one of the hydrogen atoms of the lower alkyl group is replaced by a halogen atom, preferably fluoro or chloro, most preferably fluoro. Among the preferred halogenated lower alkyl groups are trifluoromethyl, difluoromethyl, difluoroethyl, fluoromethyl and chloromethyl, with trifluoromethyl and difluoroethyl being especially preferred.

The term "lower halogenalkoxy" or "halogen-$C_{1-7}$-alkoxy" refers to lower alkoxy groups as defined above wherein at least one of the hydrogen atoms of the lower alkoxy group is replaced by a halogen atom, preferably fluoro or chloro, most preferably fluoro. Among the preferred halogenated lower alkyl groups are trifluoromethoxy, difluoromethoxy, fluoromethoxy and chloromethoxy, with trifluoromethoxy being especially preferred.

The term "lower hydroxyalkyl" or "hydroxy-$C_{1-7}$-alkyl" refers to lower alkyl groups as defined above wherein at least one of the hydrogen atoms of the lower alkyl group is replaced by a hydroxy group. Examples of lower hydroxyalkyl groups are hydroxymethyl or hydroxyethyl, but also groups having two hydroxy groups such as 1,3-dihydroxy-2-propyl.

The term "lower hydroxyalkoxy" or "hydroxy-$C_{1-7}$-alkoxy" refers to lower alkoxy groups as defined above wherein at least one of the hydrogen atoms of the lower alkoxy group is replaced by a hydroxy group. Examples of lower hydroxyalkoxy groups are hydroxymethoxy or hydroxyethoxy.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, preferably hydrochloric acid, and organic acids such as acetic acid, propionic acid, glycolic acid, pyruvic acid, oxylic acid, maleic acid, malonic acid, salicylic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein and the like. In addition these salts may be prepared from addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyamine resins and the like. The compound of formula I can also be present in the form of zwitterions. Particularly preferred pharmaceutically acceptable salts of compounds of formula I are the hydrochloride salts.

The compounds of formula I can also be solvated, e.g., hydrated. The solvation can be effected in the course of the manufacturing process or can take place, e.g., as a consequence of hygroscopic properties of an initially anhydrous compound of formula I (hydration). The term "pharmaceutically acceptable salts" also includes physiologically acceptable solvates.

"Isomers" are compounds that have identical molecular formulae but that differ in the nature or the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images are termed "enantiomers", or sometimes optical isomers.

A carbon atom bonded to four nonidentical substituents is termed a "chiral center".

In detail, the present invention relates to compounds of the general formula I

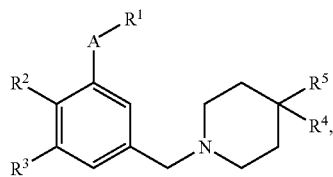

Wherein
A is —O— or —NH—;
$R^1$ is selected from the group consisting of $C_{2-7}$-alkyl, $C_{2-7}$-alkenyl, $C_{3-7}$-alkinyl, $C_{3-7}$-cycloalkyl, halogen-$C_{1-7}$-alkyl, $C_{1-7}$-alkoxy-$C_{1-7}$-alkyl and benzyl;
$R^2$ is selected from the group consisting of hydrogen, $C_{1-7}$-alkyl,
hydroxy, $C_{1-7}$-alkoxy, $C_{2-7}$-alkenyloxy,
hydroxy-$C_{1-7}$-alkoxy, $C_{1-7}$-alkoxy-$C_{1-7}$-alkoxy,
—O-benzyl, —O—$C_{3-7}$-cycloalkyl,
halogen, halogen-$C_{1-7}$-alkyl, halogen-$C_{1-7}$-alkoxy,
amino, pyrrolyl, imidazolyl,
—C(O)OR$^6$, wherein $R^6$ is $C_{1-7}$-alkyl, and
unsubstituted phenyl or phenyl substituted by one to three groups independently selected from $C_{1-7}$-alkyl, halogen and $C_{1-7}$-alkoxy;
$R^3$ is hydrogen or $C_{1-7}$-alkoxy;
$R^4$ is —NH—CO—$R^7$, wherein $R^7$ is a ring selected from phenyl or pyridyl, said ring being unsubstituted or substituted by one or two groups selected from $C_{1-7}$-alkyl or halogen;
$R^5$ is —CO—NH$_2$ or —CN;
or $R^4$ and $R^5$ are bonded to each other to form a ring together with the carbon atom to which they are attached, and $R^4$ and $R^5$ together are:
—NH—C(O)—NH—C(O)—,
—C(O)—NR$^8$—CH$_2$—CH$_2$—, wherein $R^8$ is phenyl, or
—N=CR$^9$—NH—C(O)—, wherein $R^9$ is phenyl;
and pharmaceutically acceptable salts thereof.

Preferred compounds of formula I of the present invention are also those, wherein A is O.

A further group of compounds of formula I are those, wherein A is NH.

Also preferred are compounds of formula I according to the invention, wherein $R^1$ is selected from the group consisting of $C_{2-7}$-alkyl, $C_{2-7}$-alkenyl, $C_{3-7}$-cycloalkyl and halogen-$C_{1-7}$-alkyl.

Especially preferred are those compounds of formula I, wherein $R^1$ is selected from the group consisting of ethyl, propyl, isopropyl, allyl, 2-fluoroethyl, isobutyl and cyclopentyl, with those compounds, wherein $R^1$ is ethyl, being most preferred.

Further preferred compounds of formula I according to the present invention are those, wherein $R^2$ is selected from the group consisting of hydrogen, $C_{1-7}$-alkyl,
$C_{1-7}$-alkoxy, $C_{2-7}$-alkenyloxy,
—O-benzyl, —O—$C_{3-7}$-cycloalkyl,
halogen, halogen-$C_{1-7}$-alkyl, halogen-$C_{1-7}$-alkoxy,
amino, pyrrolyl, imidazolyl, and
unsubstituted phenyl or phenyl substituted by one to three groups independently selected from $C_{1-7}$-alkyl, halogen and $C_{1-7}$-alkoxy.

More preferred are those compounds of formula I, wherein $R^2$ is selected from the group consisting of group consisting of hydrogen, $C_{1-7}$-alkoxy, $C_{2-7}$-alkenyloxy, halogen, halogen-$C_{1-7}$-alkoxy, pyrrolyl and phenyl substituted by halogen, with those compounds, wherein $R^2$ is halogen, being especially preferred. Most preferably, $R^2$ is chloro.

Furthermore, compounds of formula I of the present invention are preferred, wherein $R^3$ is $C_{1-7}$-alkoxy. More preferably, $R^3$ is ethoxy or isopropyloxy.

Also preferred are compounds of formula I, wherein $R^3$ is hydrogen.

A group of preferred compounds of formula I according to the present invention are those, wherein $R^4$ and $R^5$ are bonded to each other to form a ring together with the carbon atom they are attached to and $R^4$ and $R^5$ together are
—NH—C(O)—NH—C(O)—. These are compounds of the formula Ia:

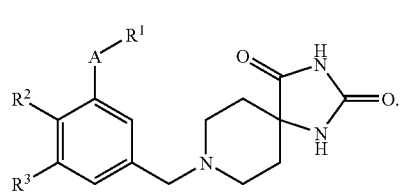

A further group of preferred compounds of formula I according to the present invention are those, wherein $R^4$ and $R^5$ are bonded to each other to form a ring together with the carbon atom they are attached to and $R^4$ and $R^5$ together are —C(O)—NR$^8$—CH$_2$—CH$_2$—, wherein $R^8$ is phenyl. These are compounds of the formula Ib:

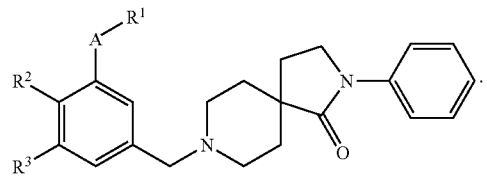

Another group of preferred compounds of formula I according to the present invention are those, wherein $R^4$ and $R^5$ are bonded to each other to form a ring together with the carbon atom they are attached to and $R^4$ and $R^5$ together are —N=CR$^9$—NH—C(O)—, wherein $R^9$ is phenyl. These are compounds of the formula Ic:

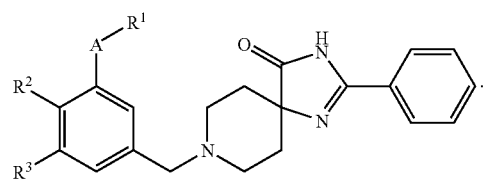

Furthermore, compounds of formula I according to the invention are preferred, wherein $R^4$ is —NH—CO—$R^7$, wherein $R^7$ is a ring selected from phenyl or pyridyl, said ring being unsubstituted or substituted by one or two groups selected from $C_{1-7}$-alkyl or halogen, and $R^5$ is —CO—$NH_2$ or —CN.

Especially preferred are compounds of formula I, wherein $R^4$ is —NH—CO—$R^7$, wherein $R^7$ is phenyl, said phenyl ring being unsubstituted or substituted by one or two groups selected from $C_{1-7}$-alkyl or halogen, with those compounds being most preferred, wherein $R^7$ is 4-chlorophenyl.

Also especially preferred are compounds of formula I according to the invention, wherein $R^4$ is —NH—CO—$R^7$ and wherein $R^7$ is pyridyl, said pyridyl ring being unsubstituted or substituted by one or two groups selected from $C_{1-7}$-alkyl or halogen.

Furthermore, compounds of formula I according to the invention are preferred, wherein $R^5$ is —CO—$NH_2$. These are compounds of the formula Id:

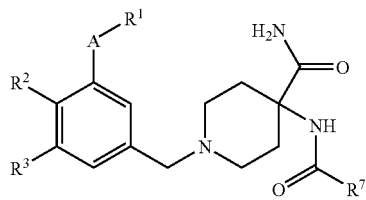

Id

Especially preferred are compounds of formula Id, wherein $R^7$ is phenyl, said phenyl ring being unsubstituted or substituted by one or two groups selected from $C_{1-7}$-alkyl or halogen.

Another group of preferred compounds of formula I according to the invention are those, wherein $R^5$ is —CN. These are compounds of formula Ie:

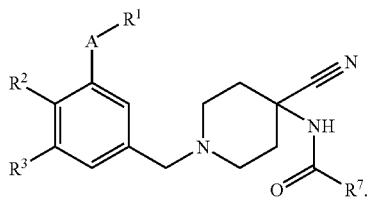

Ie

Especially preferred are compounds of formula Ie, wherein $R^7$ is pyridyl, said pyridyl ring being unsubstituted or substituted by one or two groups selected from $C_{1-7}$-alkyl or halogen. Most preferably, $R^7$ is 3-pyridyl.

Examples of preferred compounds of formula I are the following:
8-(3-ethoxy-4-methyl-benzyl)-1,3,8-triaza-spiro[4.5]decane-2,4-dione,
8-(4-chloro-3-ethoxy-benzyl)-1,3,8-triaza-spiro[4.5]decane-2,4-dione,
8-(3-isobutoxy-4-methoxy-benzyl)-1,3,8-triaza-spiro[4.5]decane-2,4-dione,
8-(3,5-diisopropoxy-benzyl)-1,3,8-triaza-spiro[4.5]decane-2,4-dione,
8-(4-chloro-3,5-diethoxy-benzyl)-1,3,8-triaza-spiro[4.5]decane-2,4-dione,
8-(4-bromo-3,5-diethoxy-benzyl)-1,3,8-triaza-spiro[4.5]decane-2,4-dione,
8-(3,5-diethoxy-4-pyrrol-1-yl-benzyl)-1,3,8-triaza-spiro[4.5]decane-2,4-dione,
8-(2,6-diethoxy-4'-fluoro-biphenyl-4-ylmethyl)-1,3,8-triaza-spiro[4.5]decane-2,4-dione,
8-(4-chloro-3-ethoxy-benzyl)-2-phenyl-2,8-diaza-spiro[4.5]decan-1-one,
8-(3,5-diethoxy-4-fluoro-benzyl)-2-phenyl-2,8-diaza-spiro[4.5]decan-1-one,
8-(4-chloro-3,5-diethoxy-benzyl)-2-phenyl-2,8-diaza-spiro[4.5]decan-1-one,
8-(4-amino-3,5-diethoxy-benzyl)-2-phenyl-2,8-diaza-spiro[4.5]decan-1-one,
8-(3,5-diethoxy-4-pyrrol-1-yl-benzyl)-2-phenyl-2,8-diaza-spiro[4.5]decan-1-one,
8-(2,6-diethoxy-4'-fluoro-biphenyl-4-ylmethyl)-2-phenyl-2,8-diaza-spiro[4.5]decan-1-one,
8-(3-ethoxy-4-methyl-benzyl)-2-phenyl-1,3,8-triaza-spiro[4.5]dec-1-en-4-one,
8-(3-ethoxy-4-fluoro-benzyl)-2-phenyl-1,3,8-triaza-spiro[4.5]dec-1-en-4-one,
8-(4-chloro-3-ethoxy-benzyl)-2-phenyl-1,3,8-triaza-spiro[4.5]dec-1-en-4-one,
8-(3-ethoxy-4-hydroxy-benzyl)-2-phenyl-1,3,8-triaza-spiro[4.5]dec-1-en-4-one,
8-(3-ethoxy-4-methoxy-benzyl)-2-phenyl-1,3,8-triaza-spiro[4.5]dec-1-en-4-one,
8-(3,4-diethoxy-benzyl)-2-phenyl-1,3,8-triaza-spiro[4.5]dec-1-en-4-one,
8-(4-allyloxy-3-ethoxy-benzyl)-2-phenyl-1,3,8-triaza-spiro[4.5]dec-1-en-4-one,
8-(3-ethoxy-4-isopropoxy-benzyl)-2-phenyl-1,3,8-triaza-spiro[4.5]dec-1-en-4-one,
8-(3-ethoxy-4-isobutoxy-benzyl)-2-phenyl-1,3,8-triaza-spiro[4.5]dec-1-en-4-one,
8-(4-cyclopentyloxy-3-ethoxy-benzyl)-2-phenyl-1,3,8-triaza-spiro[4.5]dec-1-en-4-one,
8-(4-benzyloxy-3-ethoxy-benzyl)-2-phenyl-1,3,8-triaza-spiro[4.5]dec-1-en-4-one,
8-(4-difluoromethoxy-3-ethoxy-benzyl)-2-phenyl-1,3,8-triaza-spiro[4.5]dec-1-en-4-one,
8-(4-methoxy-3-propoxy-benzyl)-2-phenyl-1,3,8-triaza-spiro[4.5]dec-1-en-4-one,
8-(3-isopropoxy-4-methoxy-benzyl)-2-phenyl-1,3,8-triaza-spiro[4.5]dec-1-en-4-one,
8-[3-(2-fluoro-ethoxy)-4-methoxy-benzyl]-2-phenyl-1,3,8-triaza-spiro[4.5]dec-1-en-4-one,
8-(3-allyloxy-4-methoxy-benzyl)-2-phenyl-1,3,8-triaza-spiro[4.5]dec-1-en-4-one,
8-(3-butoxy-4-methoxy-benzyl)-2-phenyl-1,3,8-triaza-spiro[4.5]dec-1-en-4-one,
8-(3-isobutoxy-4-methoxy-benzyl)-2-phenyl-1,3,8-triaza-spiro[4.5]dec-1-en-4-one,
8-(3-cyclopentyloxy-4-methoxy-benzyl)-2-phenyl-1,3,8-triaza-spiro[4.5]dec-1-en-4-one,
8-(3,5-diethoxy-benzyl)-2-phenyl-1,3,8-triaza-spiro[4.5]dec-1-en-4-one,
8-(3,5-diisopropoxy-benzyl)-2-phenyl-1,3,8-triaza-spiro[4.5]dec-1-en-4-one,
8-(3,5-diethoxy-4-fluoro-benzyl)-2-phenyl-1,3,8-triaza-spiro[4.5]dec-1-en-4-one,
8-(4-chloro-3,5-diethoxy-benzyl)-2-phenyl-1,3,8-triaza-spiro[4.5]dec-1-en-4-one,
8-(4-bromo-3,5-diethoxy-benzyl)-2-phenyl-1,3,8-triaza-spiro[4.5]dec-1-en-4-one,
8-(3,5-diethoxy-4-pyrrol-1-yl-benzyl)-2-phenyl-1,3,8-triaza-spiro[4.5]dec-1-en-4-one, 4-(4-chloro-benzoylamino)-1-(4-chloro-3-ethoxy-benzyl)-piperidine-4-carboxylic acid amide, 4-(4-chloro-benzoylamino)-1-(3,5-diethoxy-4-fluoro-benzyl)-piperidine-4-carboxylic acid amide, 4-(4-chloro-benzoylamino)-1-(4-chloro-3,5-diethoxy-benzyl)-piperidine-4-carboxylic acid amide, N-[4-cyano-1-(3-ethoxy-4-methyl-benzyl)-piperidin-4-yl]-5-methyl-nicotinamide, N-[4-cyano-1-(3,5-diethoxy-4-fluoro-benzyl)-piperidin-4-yl]-5-methyl-nicotinamide, 6-chloro-N-[1-(4-chloro-3,5-diethoxy-benzyl)-4-cyano-piperidin-4-yl]-nicotinamide, 6-chloro-N-[4-cyano-1-(2,6-diethoxy-4'-fluoro-biphenyl-4-ylmethyl)-piperidin-4-yl]-nicotinamide, and pharmaceutically acceptable salts thereof.

Especially preferred are the following compounds of formula I of the present invention:

8-(4-chloro-3,5-diethoxy-benzyl)-1,3,8-triaza-spiro[4.5]decane-2,4-dione, 8-(4-bromo-3,5-diethoxy-benzyl)-1,3,8-triaza-spiro[4.5]decane-2,4-dione, 8-(3,5-diethoxy-4-pyrrol-1-yl-benzyl)-1,3,8-triaza-spiro[4.5]decane-2,4-dione, 8-(2,6-diethoxy-4'-fluoro-biphenyl-4-ylmethyl)-1,3,8-triaza-spiro[4.5]decane-2,4-dione, 8-(3-ethoxy-4-methyl-benzyl)-2-phenyl-1,3,8-triaza-spiro[4.5]dec-1-en-4-one, 8-(4-chloro-3-ethoxy-benzyl)-2-phenyl-1,3,8-triaza-spiro[4.5]dec-1-en-4-one, 8-(4-chloro-3,5-diethoxy-benzyl)-2-phenyl-1,3,8-triaza-spiro[4.5]dec-1-en-4-one, 8-(4-bromo-3,5-diethoxy-benzyl)-2-phenyl-1,3,8-triaza-spiro[4.5]dec-1-en-4-one, 8-(3,5-diethoxy-4-pyrrol-1-yl-benzyl)-2-phenyl-1,3,8-triaza-spiro[4.5]dec-1-en-4-one, 4-(4-chloro-benzoylamino)-1-(4-chloro-3,5-diethoxy-benzyl)-piperidine-4-carboxylic acid amide, 6-chloro-N-[4-cyano-1-(2,6-diethoxy-4'-fluoro-biphenyl-4-ylmethyl)-piperidin-4-yl]-nicotinamide, and pharmaceutically acceptable salts thereof.

Furthermore, the pharmaceutically acceptable salts of the compounds of formula I individually constitute preferred embodiments of the present invention.

Compounds of formula I can have one or more asymmetric carbon atoms and can exist in the form of optically pure enantiomers, mixtures of enantiomers such as, for example, racemates, optically pure diastereoisomers, mixtures of diastereoisomers, diastereoisomeric racemates or mixtures of diastereoisomeric racemates. The optically active forms can be obtained for example by resolution of the racemates, by asymmetric synthesis or asymmetric chromatography (chromatography with a chiral adsorbens or eluant). The invention embraces all of these forms.

It will be appreciated, that the compounds of general formula I in this invention may be derivatized at functional groups to provide derivatives which are capable of conversion back to the parent compound in vivo. Physiologically acceptable and metabolically labile derivatives, which are capable of producing the parent compounds of general formula I in vivo are also within the scope of this invention.

A further aspect of the present invention is the process for the manufacture of compounds of formula I as defined above, which process comprises a) reacting a piperidine of the formula

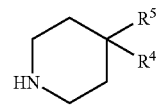

II wherein $R^4$ and $R^5$ are as defined herein before,
with an aldehyde of the formula

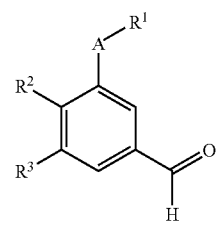

III wherein A and $R^1$ to $R^3$ are as defined herein before,
by employing a reducing agent to obtain a compound of the formula

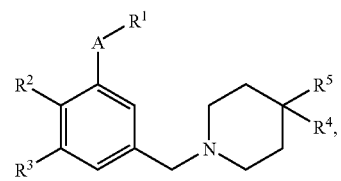

I and, if desired, converting the compound of formula I into a pharmaceutically acceptable salt; or, alternatively, b) alkylating a piperidine of the formula

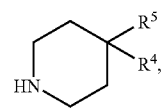

II wherein $R^4$ and $R^5$ are as defined herein before,
with a compound of the formula

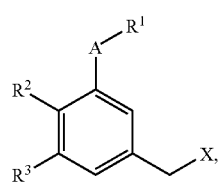

IV wherein A and $R^1$ to $R^3$ are as defined herein before and X is a leaving group, under basic conditions to obtain a compound or formula

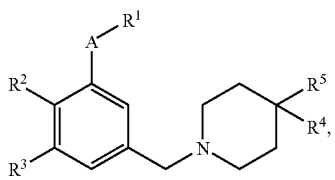

and, if desired, converting the compound of formula I into a pharmaceutically acceptable salt; or, alternatively, c) reacting a compound of the general formula

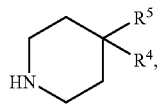

wherein $R^4$ and $R^5$ are as defined herein before, with a compound of the formula

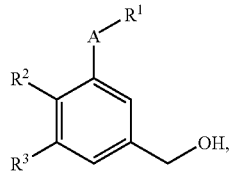

wherein A and $R^1$ to $R^3$ are as defined herein before, in the presence of a trialkylphosphine and a diazo-compound to obtain a compound of the formula

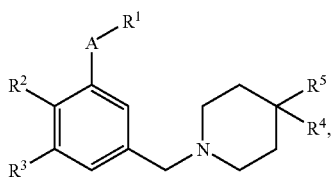

and, if desired, converting the compound of formula I into a pharmaceutically acceptable salt.

The invention further relates to compounds of formula I as defined above, when manufactured according to a process as defined herein before.

Suitable reducing agents are preferably selected from the group consisting of pyridine-$BH_3$ complex, $NaBH(OAc)_3$ and $NaCNBH_3$. The reaction can be carried out under acidic conditions by using a Broensted acid such as acetic acid or formic acid or a Lewis acid (e.g., $Ti(iPrO)_4$, $ZnCl_2$) or under buffered conditions (e.g., in the presence of acetic acid and a tertiary amine like N-ethyldiisopropylamine or triethylamine) in a suitable solvent such as dichloromethane, dichloroethane, ethanol or isopropanol (or mixtures thereof) at ambient or elevated temperatures using conventional heating or heating by microwave irradiation. Suitable leaving groups X are halides, mesylates or tosylates or alcohols transformed into another leaving group. Preferred leaving groups are selected from the group consisting of iodide, bromide, methanesulfonate and chloride.

Suitable trialkylphosphines are tributylphosphine and triphenylphosphine. Preferred diazocompounds are diethyl azodicarboxalate (DEAD), diisopropyl azodicarboxylate (DIAD) or di-tert-butyl azodicarboxylate.

As described above, the compounds of formula I of the present invention can be used as medicaments for the treatment and/or prevention of diseases which are associated with the modulation of SST receptors subtype 5.

Diseases which are associated with the modulation of SST receptors subtype 5 are such diseases as diabetes mellitus, particularly type II diabetes mellitus, impaired fasting glucose, impaired glucose tolerance, micro- and macrovascular diabetic complications, post transplantation diabetes mellitus in patients having type I diabetes mellitus, gestational diabetes, obesity, inflammatory bowel diseases such as Crohn's disease or ulcerative colitis, malabsorption, autoimmune diseases such as rheumatoid arthritis, osteoarthritis, psoriasis and other skin disorders, and immunodeficiencies. Microvascular diabetic complications include diabetic nephropathy and diabetic retinopathy, whereas macrovascular diabetes-associated complications lead to an increased risk for myocardial infarction, stroke and limb amputations.

The use as medicament for the treatment and/or prevention of diabetes mellitus, particularly type II diabetes mellitus, impaired fasting glucose or impaired glucose tolerance is preferred.

The invention therefore also relates to pharmaceutical compositions comprising a compound as defined above and a pharmaceutically acceptable carrier and/or adjuvant.

Further, the invention relates to compounds as defined above for use as therapeutically active substances, particularly as therapeutic active substances for the treatment and/or prevention of diseases which are associated with the modulation of SST receptors subtype 5.

In another embodiment, the invention relates to a method for the treatment and/or prevention of diseases which are associated with the modulation of SST receptors subtype 5, which method comprises administering a compound of formula I to a human or animal. The method for the treatment and/or prevention of diabetes mellitus, particularly type II diabetes mellitus, impaired fasting glucose or impaired glucose tolerance, is most preferred.

The invention further relates to the use of compounds as defined above for the treatment and/or prevention of diseases which are associated with the modulation of SST receptors subtype 5.

In addition, the invention relates to the use of compounds as defined above for the preparation of medicaments for the treatment and/or prevention of diseases which are associated with the modulation of SST receptors subtype 5. Preferred examples of such diseases are diabetes mellitus, particularly type II diabetes mellitus, impaired fasting glucose or impaired glucose tolerance.

The compounds of formula I can be manufactured by the methods given below, by the methods given in the examples or by analogous methods. Appropriate reaction conditions for the individual reaction steps are standard reactions and are known to a person skilled in the art. Starting materials are either commercially available or can be prepared by methods analogous to the methods given below, by methods described in references cited in the text or in the examples, or by methods known in the art.

The synthesis of compounds with the general structure I, particularly compounds according to formula Ia to Ie, are described in Schemes 1 to 6.

The synthesis of compounds of compounds according to formula Ia, can be accomplished according to Scheme 1.

Target compounds of formula Ia can be obtained by reductive N-alkylation of free piperidines 1 with aldehydes 2 in the presence of a reducing agent such as pyridine-$BH_3$ complex, $NaBH(OAc)_3$ or $NaCNBH_3$ under acidic conditions (e.g., acetic acid, formic acid), by using a Lewis acid (e.g., $Ti(iPrO)_4$, $ZnCl_2$) or under buffered conditions, e.g., in the presence of acetic acid and a tertiary amine like N-ethyldiisopropylamine or triethylamine, in a suitable solvent such as dichloromethane (DCM), dichloroethane, ethanol or isopropanol (or mixtures thereof) at ambient or elevated tempera tures using conventional heating or heating by microwave irradiation (Scheme 1, step a). Piperidine 1 can be prepared according to literature methods (K. H. Bleicher, Y. Wüthrich, M. De Boni, S. Kolczewski, T. Hoffmann, A. J. Sleight *Bioorg. Med. Chem. Lett.* 2002, 12, 2519-2522) and might thereby be used either as salt, e.g., hydrochloride or hydrobromide, or as the corresponding free amine.

the like (Scheme 1, step b). There is no particular restriction on the nature of the solvent to be employed, provided that it has no adverse effect on the reaction or the reagents involved and that it can dissolve the reagents, at least to some extent. The reaction can take place over a wide range of temperatures ranging from ambient temperature to the reflux temperature of the solvent employed.

Scheme 1

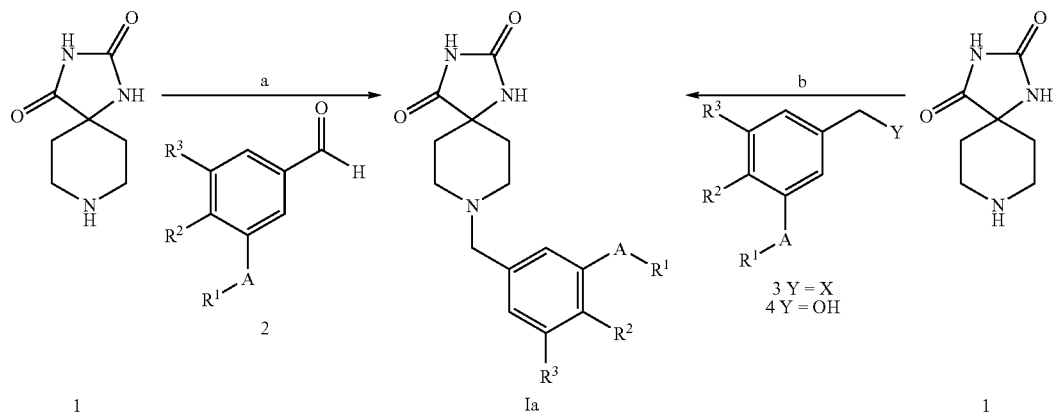

Target compounds of formula Ia might also be manufactured by direct alkylation of piperidines 1 with suitable halides, mesylates, tosylates or alcohols transformed into any other suitable leaving group X of general structure 3 in a solvent such as DMF, dichloromethane, dichloroethane or acetone at ambient or elevated temperatures using conventional heating or heating by microwave irradiation with the addition of a suitable tertiary amine base (e.g., triethylamine, N-ethyldiisopropylamine) or an inorganic base (e.g., $Cs_2CO_3$, $K_2CO_3$) or by analogous alkylation reactions. Alternatively, target structures of formula Ia might be accessible by Mitsunobu reaction (D. L. Hughes, The Mitsunobu Reaction, Using a similar strategy, target compounds of formula Ib are accessible using either reductive alkylation of piperidine 5 with aldehydes 2 (Scheme 2, step a) or direkt alkylation of 5 with intermediates 3 or 4 under conditions as previously discussed (Scheme 2, step b). 2,8-Diaza-spiro[4.5]decan-1-one 5 is either commercially available (Ennova MedChem Group, Inc., USA) or can be prepared as described in the literature (R. Süess *Helv. Chim. Acta* 1977, 60, 1650-1656).

Scheme 2

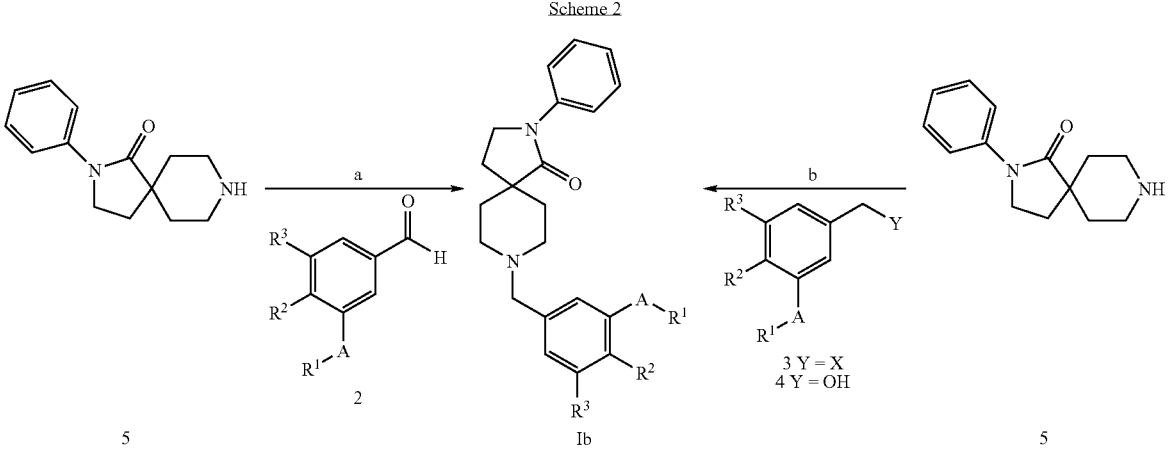

in *Organic Reactions*, Volume 42, 1992, John Wiley & Sons, New York; pp. 335-656) applying alcohols 4 activated by a mixture of a phosphine like a trialkylphosphine such as tributylphosphine ($(n-Bu)_3P$), triphenylphosphine ($Ph_3P$) and the like and a diazo-compound like diethyl azodicarboxylate (DEAD), diisopropyl azodicarboxylate (DIAD) or di-tert-butyl azodicarboxylate and the like in a solvent commonly used for such transformations like THF, toluene, DCM and Target compounds of general structures Ic can be accomplished by a strategy using either reductive alkylation of spiro derivative 6 with aldehydes 2 (Scheme 3, step a) or direkt alkylation of 6 with intermediates 3 or 4 under conditions as previously discussed (Scheme 3, step b). 2-Phenyl-1,3,8-triaza-spiro[4.5]dec-1-en-4-one 6 can be prepared as described in WO 03/104 236 A1 (Bristol-Myers Squibb Company).

Scheme 3

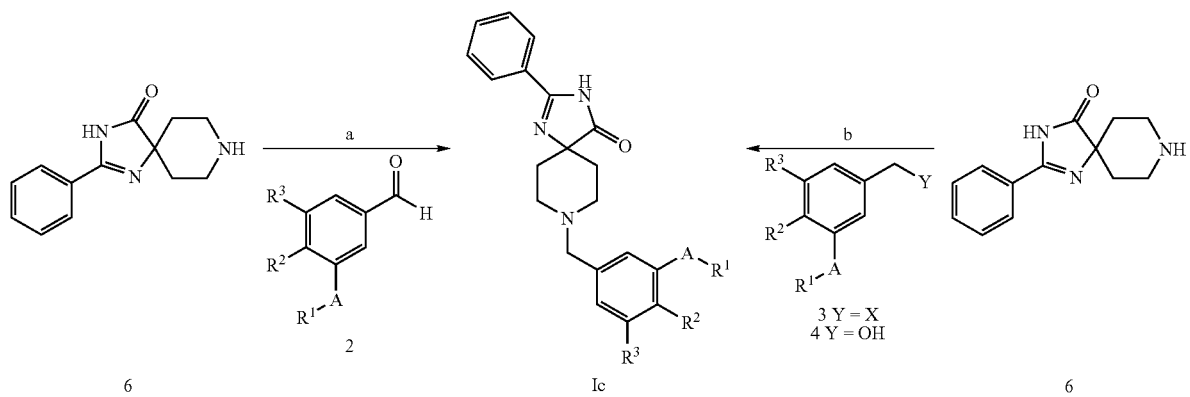

Target compounds of general structures Id can be prepared from suitably protected 4-amino-4-cyano-piperidines 7 (for protecting groups see Protective Groups in Organic Synthesis, T. W. Greene, Wiley-Interscience 1999) via coupling with various types of acids or acid chlorides by means of well known coupling methods to give amides 8 (Scheme 4, step a), wherein B means CH or N. Typically, the amide bond formation of piperidine 7 with a benzoyl chloride to give intermediates 8 is conducted in the presence of a tertiary amine base (e.g., triethylamine, N-ethyldiisopropylamine) in an inert solvent like DCM or toluene and the like at room or elevated temperature (Scheme 4, step a). Suitable coupling agents for the reaction of carboxylic acids with amines are N,N'-carbonyldiimidazole (CDI), N,N'-dicyclohexylcarbodiimide (DCC), 1-(3-dimethyl-aminopropyl)-3-ethylcarbodiimide hydrochloride (EDCI), 1-[bis(dimethylamino)methylene]-1H-1,2,3-triazolo[4,5-b]pyridinium-3-oxide hexafluorophosphate (HATU), 1-hydroxy-1,2,3-benzotriazole (HOBT), O-benzotriazol-1-yl-N,N,N',N'-tetramethyl-uronium tetrafluoroborate (TBTU) and the like. Preferred coupling agents are 1-(3-dimethylaminopropyl)-3-ethylcarbodiimide hydrochloride (EDCI) or N,N'-carbonyldiimidazole (CDI), typically in a solvent such as dimethylformamide (DMF) or dichloroethane (DCE) at room or elevated temperatures.

Removal of the alkyloxycarbonyl protecting group in cyano piperidine 8 can be conducted under strong acid catalysis (Scheme 4, step b) to provide free amines 9. Depending on the reaction conditions (e.g., reaction time, temperature and presence of traces of water) of the deprotection step of piperidine 8 partial hydrolysis of the cyano group in 9b to the primary amide 9a might occur. In such cases where mixtures of cyano 9b and amide compounds 9a were obtained the product mixture was directly used for the subsequent reductive amination step without further purification. Finally, reductive alkylation of the free piperidine 9a with aldehydes 2 gives access to target compounds Id (Scheme 4, step c). During this transformation step further hydrolysis of the cyano to the primary amide bond might occur. Preparative HPLC or silica column chromatography allows the isolation and purification of the targeted primary amide derivatives.

Scheme 4

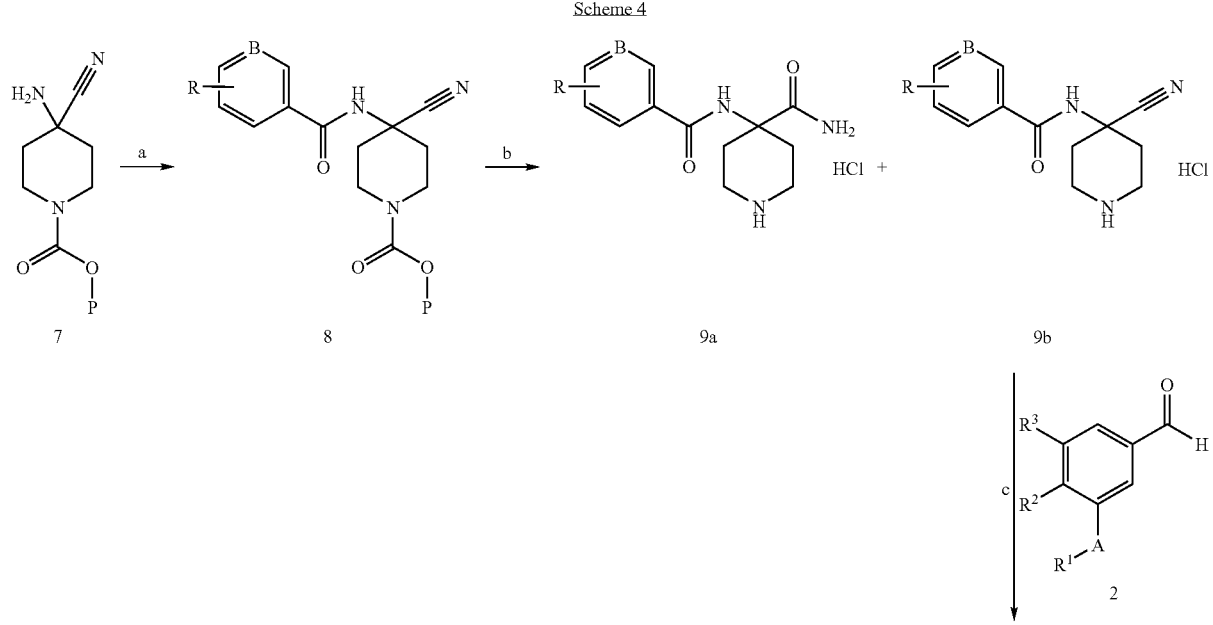

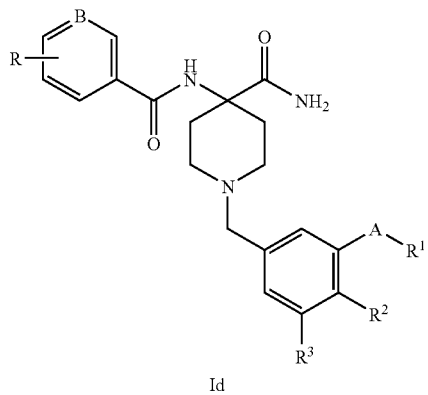

Id

P = —CH$_2$CH$_3$ or —C(CH$_3$)$_3$

Target compounds of general structures Ie are accessible via coupling of cyano piperidines 9b with aldehydes 2 as previously described. Again purification of the final compound with prep. HPLC or silica column chromatography allows isolating the targeted primary cyano derivatives.

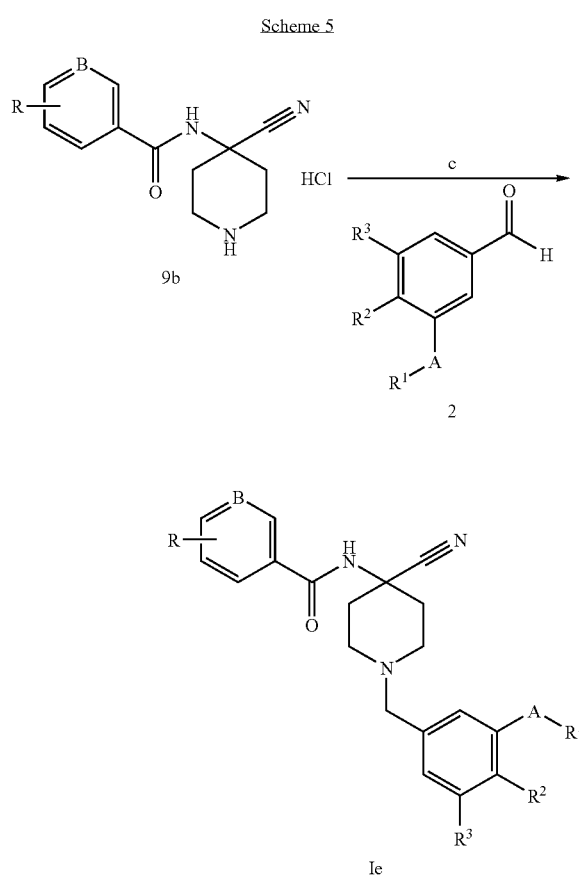

Scheme 5

Synthesis of Aldehyde Intermediates

The requisite aldehyde partners are either commercially available or can be derived by alkylation with alkyl halides, alkyl mesylates, alkyl tosylates or alcohols transformed into another suitable leaving group in a polar solvent such as DMF (N,N-dimethylformamide) or acetone and a suitable base (e.g., Cs$_2$CO$_3$, K$_2$CO$_3$) at room temperature or elevated temperatures, by Mitsunobu reaction with alcohols activated by a mixture of triphenylphosphine and diethyl azadicarboxylate, or by analogous alkylation of the phenolic carboxylic esters or acids of formula 10 (Scheme 6, step a). Reduction of the esters of formula 11 by a suitable reducing agent (e.g., diisobutylaluminum hydride at low temperature or with LiAlH$_4$ at low, elevated or ambient temperature) in a solvent such as THF provides the corresponding benzylalcohols of formula 12 (Scheme 6, step b), which can then be oxidized to the aldehydes of formula 13, preferably with activated MnO$_2$ as oxidant in DCM (Scheme 6, step c).

Alternatively the introduction of the side-chain can be accomplished by direct alkylation (sequential for unsymmetrical compounds) of the phenolic benzaldehydes of formula 13 providing the desired compounds of formula 2 directly (Scheme 6, step d).

A further well-established route towards the synthesis of benzylaldehydes of formula 15 consists in the reduction of the corresponding benzonitriles of formula 14 by a suitable reducing agent such as diisobutylaluminum hydride at low temperature in a non-protic polar solvent (e.g., THF; Scheme 6, step e).

Additional syntheses of aldehydes of formula II are described in the examples.

Scheme 6

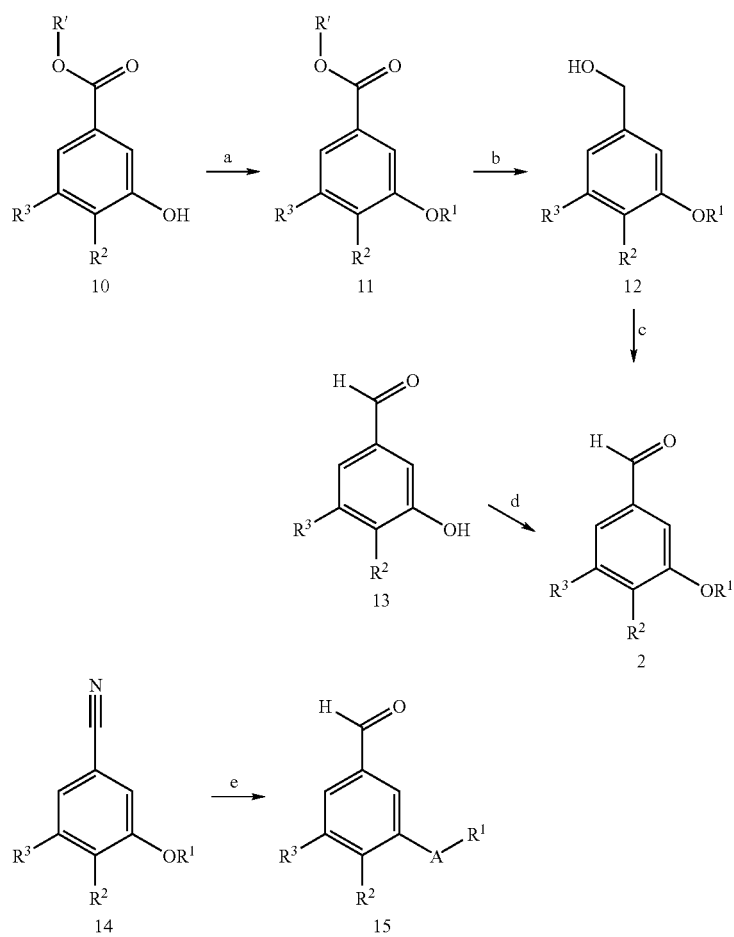

As described hereinbefore, it has been found that the compounds of formula I possess pharmaceutical activity, in particular they are modulators of somatostatin receptor activity. More particularly, the compounds of the present invention have been found to be antagonists of the somatostatin receptor subtype 5 (SSTR5).

The following tests were carried out in order to determine the activity of the compounds of formula I.

A CHO cell line stably transfected with a plasmid encoding the human subtype 5 somatostatin receptor (GenBank accession number D16827) was obtained from Euroscreen. Cells were cultured and used for binding and functional assays.

Membranes of these cells were prepared by sonication in the presence of protease inhibitors and subsequent fractionating centrifugation. The protein concentration in the membrane preparation was determined using a commercial kit (BCA kit, Pierce, USA). Membranes were stored at −80° C. until use. After thawing membranes were diluted in assay buffer (50 mM Tris-HCl at pH 7.4, 5 mM $MgCl_2$ and 0.20% BSA) and subjected to dounce homogenization.

For binding studies, 0.1 mL membrane suspension, corresponding to approximately $6\times10^{-15}$ mol receptor, was incubated for 1 h at room temperature with 0.05 nM $^{125}$I-labeled tracer (11-Tyr somatostatin-14, Perkin-Elmer) and either test compounds in varying concentrations or, for the determination of non-specific binding, 0.001 mM non-labeled somatostatin-14. The incubation was stopped by filtration through GF/B glassfiber filters and washing with ice-cold wash buffer (50 mM Tris-HCl at pH 7.4). The bound radioactivity was measured after application of a scintillation cocktail (Microscint 40) and expressed as disintegrations per minute (dpm).

The receptor concentration was determined in a prior saturation experiment where a fixed, arbitrary amount of membranes was incubated with a concentration range of radio-labeled tracer. This allows estimating the total number of specific binding sites per amount of protein (i.e., $B_{max}$), typically between 1 and 5 pmol/mg.

The concentration of the test compound required to result in half maximal inhibition of binding of the radio-labeled tracer ($IC_{50}$) was estimated from a concentration-versus-dpm graph. The binding affinity ($K_i$) was calculated from the $IC_{50}$ by applying the Cheng-Prussoff equation for single binding sites.

For functional experiments, 50'000 cells were incubated in Krebs Ringer HEPES buffer (115 mM NaCl, 4.7 mM KCl, 2.56 mM $CaCl_2$, 1.2 mM $KH_2PO_4$, 1.2 mM $MgSO_4$, 20 mM $NaHCO_3$ and 16 mM HEPES, adjusted to pH 7.4) supplemented with 1 mM IBMX and 0.1% BSA, then stimulated with 0.004 mM forskolin. Simultaneously with forskolin, test compounds in varying concentrations were applied. Cells were then incubated for 20 minutes at 37° C. and 5% $CO_2$. Subsequently, cells were lysed and cAMP concentration measured using a fluorescence-based commercial kit according to the manufacturer (HitHunter cAMP, DiscoverX).

The concentration of the test compound to induce a half maximal effect (i.e., $EC_{50}$) as well as the efficacy as compared to 0.15 nM somatostatin-14 were determined from concentration-versus-fluorescence (arbitrary units) graphs. For the determination of potential antagonism, 0.15 nM somatostatin-14 was applied together with the test compounds and the concentration of the test compounds to half maximally reverse the effect of somatostatin-14 (i.e., $IC_{50}$) were deduced from concentration-versus-fluorescence graphs.

The compounds of the present invention exhibit in a radioligand replacement assay $K_i$ values of 0.1 nM to 10 μM, preferably $K_i$ values of 0.1 nM to 500 nM and more preferably 0.1 nM to 100 nM for the human subtype 5 somatostatin receptor. The following table shows measured values for selected compounds of the present invention.

|  | SSTR5 $K_i$ (nmol/l) |
| --- | --- |
| Example 2 | 51 |
| Example 5 | 42 |
| Example 7 | 15 |
| Example 11 | 228 |
| Example 15 | 37 |
| Example 17 | 50 |
| Example 26 | 226 |
| Example 29 | 717 |
| Example 33 | 273 |
| Example 38 | 18 |
| Example 42 | 96 |
| Example 44 | 342 |
| Example 46 | 66 |

The compounds of formula I and their pharmaceutically acceptable salts and esters can be used as medicaments, e.g., in the form of pharmaceutical preparations for enteral, parenteral or topical administration. They can be administered, for example, perorally, e.g., in the form of tablets, coated tablets, dragées, hard and soft gelatine capsules, solutions, emulsions or suspensions, rectally, e.g., in the form of suppositories, parenterally, e.g., in the form of injection solutions or infusion solutions, or topically, e.g., in the form of ointments, creams or oils. The production of the pharmaceutical preparations can be effected in a manner which will be familiar to any person skilled in the art by bringing the described compounds of formula I and their pharmaceutically acceptable, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragées and hard gelatine capsules. Suitable carrier materials for soft gelatine capsules are, for example, vegetable oils, waxes, fats and semi-solid and liquid polyols (depending on the nature of the active ingredient no carriers are, however, required in the case of soft gelatine capsules). Suitable carrier materials for the production of solutions and syrups are, for example, water, polyols, sucrose, invert sugar and the like. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavor-improving agents, salts for varying the osmotic pressure, buffer substances, solubilizers, colorants and masking agents and antioxidants come into consideration as pharmaceutical adjuvants.

The dosage of the compounds of formula I can vary within wide limits depending on the disease to be controlled, the age and the individual condition of the patient and the mode of administration, and will, of course, be fitted to the individual requirements in each particular case. For adult patients a daily dosage of about 1 mg to about 1000 mg, especially about 1 mg to about 100 mg, comes into consideration. Depending on the dosage it is convenient to administer the daily dosage in several dosage units.

The pharmaceutical preparations conveniently contain about 0.1-500 mg, preferably 0.5-100 mg, of a compound of formula I.

The present invention will be further explained by reference to the following illustrative examples. They are, however, not intended to limit its scope in any manner.

EXAMPLES

Abbreviations

Ar=argon, DMF=N,N-dimethylformamide, DMSO=dimethyl sulfoxide, EI=electron impact (ionization), HPLC=high performance liquid chromatography, Hyflo Super Cel®=filtration aid (Fluka), ISP=ion spray positive (mode), NMR=nuclear magnetic resonance, MPLC=medium pressure liquid chromatography, MS=mass spectrum, P=protecting group, R=any group, rt=room temperature, THF=tetrahydrofuran, X=halogen.

Example 1

8-(3-Ethoxy-4-methyl-benzyl)-1,3,8-triaza-spiro[4.5]decane-2,4-dione

Step 1: 1,3,8-Triaza-spiro[4.5]decane-2,4-dione [CAS RN 13625-39-3] (Intermediate A1)

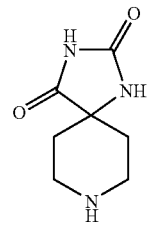

The title compound was prepared as described in K. H. Bleicher, Y. Wüthrich, M. De Boni, S. Kolczewski, T. Hoffmann, A. J. Sleight *Bioorg. Med. Chem. Lett.* 2002, 12, 2519-2522.

Step 2: 8-(3-Ethoxy-4-methyl-benzyl)-1,3,8-triaza-spiro[4.5]decane-2,4-dione

To a solution of 1,3,8-triaza-spiro[4.5]decane-2,4-dione (25.4 mg, 0.15 mmol, 1.0 equiv; intermediate A1) in ethanol (1 mL), acetic acid (72.1 mg, 1.2 mmol, 8.0 equiv) and N-ethyl diisopropylamine (77.6 mg, 0.6 mmol, 4.0 equiv) was added 3-ethoxy-4-methyl-benzaldehyde (29.6 mg, 0.18 mmol, 1.2 equiv; intermediate B10, vide infra) and the mixture stirred at 55° C. After 1 h, sodium cyanoborohydride (47.1 mg, 0.75 mmol, 5.0 equiv), dissolved in ethanol (0.5 mL), was added and the mixture stirred at 55° C. over night. Removal of the solvent under reduced pressure and purification by preparative HPLC on reversed phase eluting with a gradient of acetonitrile/water provided 8.6 mg (17%) of the title compound. MS (ISP): 338.2 [M+H]$^+$.

The 2,8-diaza-spiro[4.5]decan-1-one and 1,3,8-triaza-spiro[4.5]dec-1-en-4-one intermediates A2 and A3 were prepared as described below.

Synthesis of 2,8-Diaza-spiro[4.5]decan-1-one and 1,3,8-Triaza-spiro[4.5]dec-1-en-4-one Intermediates A2 and A3 to be used in Table 1

Intermediate A2

2-Phenyl-2,8-diaza-spiro[4.5]decan-1-one hydrochloride [CAS RN 64097-88-7]

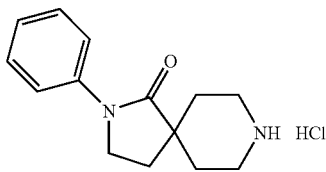

The title compound is commercially available from Ennova MedChem Group, Inc., USA.

Intermediate A3

2-Phenyl-1,3,8-triaza-spiro[4.5]dec-1-en-4-one hydrochloride

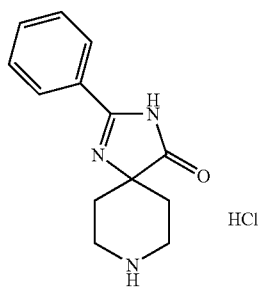

The title compound was prepared as described in WO 03/104 236 A1 (Bristol-Myers Squibb Company).

The aldehyde intermediates B1 to B16 were prepared following literature precedents or in analogy to literature precedents or as described below.

Synthesis of Aldehyde Intermediates B1 to B16 to be used in Table 1 to Table 3

Intermediate B1

4-Chloro-3-ethoxy-benzaldehyde [CAS RN 85259-46-7]

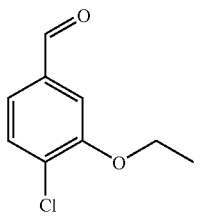

To a solution of 4-chloro-3-hydroxy-benzoic acid (3.0 g, 17.4 mmol, 1.0 equiv) in DMF (15 mL) was added K$_2$CO$_3$ (4.81 g, 34.8 mmol, 2.0 equiv) and ethyl iodide (4.03 mL, 5.97 g, 38.2 mmol, 2.2 equiv). The reaction mixture was stirred for 6 h at rt, diluted with water (20 mL) and extracted with ethyl acetate (3×50 mL). The organic phase was dried over Na$_2$SO$_4$ and concentrated to afford 3.6 g (91%) of 4-chloro-3-ethoxy-benzoic acid ethyl ester. The crude ester was then dissolved in THF (20 mL) and cooled to −78° C. under Ar. A solution of diisobutylaluminum hydride (95 mL, 95.0 mmol, 6.0 equiv; 1.0 M solution in THF) was slowly added over a time period of 15 min, the cooling bath removed after completion of addition and the reaction allowed to reach 0° C. After stirring for 1 h, the reaction was cooled to −78° C. and the excess of hydride quenched by cautious addition of a solution of 1 M HCl (10 mL). The mixture was warmed up to rt, the organic phase separated and the aqueous layer extracted with ethyl acetate (3×100 mL). The combined organic phases were dried over Na$_2$SO$_4$ and concentrated by evaporation under reduced pressure providing 2.94 g (100%) of 4-chloro-3-ethoxy-benzyl alcohol. The crude alcohol (2.94 g, 15.75 mmol, 1.0 equiv) was dissolved in dichloromethane (15 mL) and activated MnO$_2$ (5.48 g, 63.0 mmol, 4.0 equiv) was added. The reaction mixture was stirred for 16 h, after which time the reaction was filtered through Hyflo Super Cel and concentrated. The residue was purified by flash column chromatography on silica eluting with heptane/ethyl acetate (4:1) to yield 1.51 g (52%) of the title compound. $^1$H NMR (300 MHz, CDCl$_3$): δ 1.51 (t, J=7.1 Hz, 3H), 4.19 (q, J=7.1 Hz, 2H), 7.37-7.42 (m, 2H), 7.55 (d, J=9.0 Hz, 1H), 9.94 (s, 1H).

Intermediate B2

3-Isobutoxy-4-methoxy-benzaldehyde [CAS RN 57724-26-2]

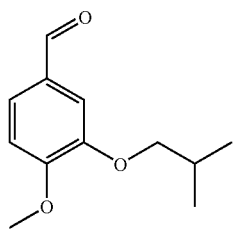

The title compound was prepared by reaction of isovanillin with 1-bromo-2-methyl propane as described in WO 04/000 806 A1 (Elbion AG).

Intermediate B3

3,5-Diisopropoxy-benzaldehyde [CAS RN 94169-64-9]

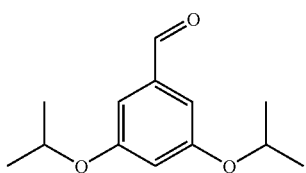

To a solution of 3,5-dihydroxy-benzaldehyde (5.0 g, 36.20 mmol, 1.0 equiv) in anhydrous DMF (30 mL) was added $K_2CO_3$ (15.0 g, 108.60 mmol, 3.0 equiv) and 2-bromo-propane (13.36 g, 10.20 mL, 108.60 mmol, 3.0 equiv) and the mixture stirred at 100° C. for 18 h. The $K_2CO_3$ was removed by filtration and the organic phase concentrated under reduced pressure. To the residue was added a sat. solution of NaCl (100 mL) and the solution extracted with ethyl acetate (3×100 mL). The combined organic phases were dried over $MgSO_4$ and the product purified by silica column chromatography using a MPLC system (CombiFlash Companion, Isco Inc.) eluting with a gradient of heptane/ethyl acetate affording 6.64 g (83%) of the title compound and 0.59 g (9%) of 3-hydroxy-5-isopropoxy-benzaldehyde. $^1H$ NMR (300 MHz, $CDCl_3$): δ 1.35 (d, J=6.1 Hz, 12H), 4.59 (hept, J=6.1 Hz, 2H), 6.66-6.68 (m, 1H), 6.96-6.97 (m, 2H), 9.88 (s, 1H). MS (ISP): 223.1 $[M+H]^+$.

Intermediate B4

4-Chloro-3,5-diethoxy-benzaldehyde

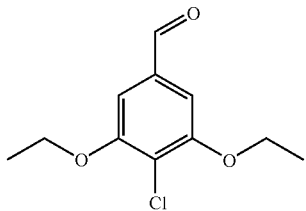

Step 1: 4-Chloro-3,5-diethoxy-benzoic acid ethyl ester

To a solution of 4-amino-3,5-diethoxy-benzoic acid ethyl ester (5.1 g, 20.13 mmol, 1.0 equiv; prepared as described in I. Kompis and A. Wick Helv. Chim. Acta 1977, 60, 3025-3034) in water (40 mL) and 37% HCl (40 mL) at 0° C. was added sodium nitrite (1.67 g, 24.16 mmol, 1.2 equiv). After 10 min, copper(I) chloride (12.0 g, 120.81 mmol, 6.0 equiv) was added, the reaction mixture stirred for an additional 5 h at 0° C. and then the ice bath removed. After stirring for 18 h, the crude reaction mixture was adjusted to pH=8 by addition of a solution of 1 M NaOH and the aqueous layer extraced with ethyl acetate (3×100 mL). The combined organic phases were dried over $MgSO_4$, concentrated by evaporation under reduced pressure and the crude material purified by silica column chromatography using a MPLC system (CombiFlash Companion, Isco Inc.) eluting with a gradient of heptane/ethyl acetate providing 5.0 g (91%) of the title compound. $^1H$ NMR (300 MHz, $CDCl_3$): δ 1.32 (t, J=7.0 Hz, 4H), 1.40 (t, J=7.0 Hz, 6H), 4.09 (q, J=7.0 Hz, 4H), 4.30 (q, J=7.0 Hz, 2H), 7.18 (s, 2H). $^{13}C$ NMR (75 MHz, $CDCl_3$): δ 13.33, 13.66, 60.29, 64.16, 105.75, 115.88, 128.25, 154.49, 165.01. MS (ISP): 273.3 $[M+H]^+$.

Step 2: (4-Chloro-3,5-diethoxy-phenyl)-methanol

To a solution of 4-chloro-3,5-diethoxy-benzoic acid ethyl ester (5.0 g, 18.33 mmol, 1.0 equiv) in dichloromethane (25 mL) was added slowly over a time period of 15 min under slight cooling to −30° C. a solution of diisobutylaluminum hydride (55.0 mL, 55.00 mmol, 3.0 equiv; 1.0 M solution in THF). After 30 min, the excess of hydride was quenched by cautious addition of methanol (10 mL) and water (2 mL). The mixture was stirred for 30 min, a solution of 1 M HCl was added and the aqueous layer extracted with ethyl acetate (3×100 mL). The combined organic phases were dried over $MgSO_4$ and concentrated by evaporation under reduced pressure providing 4.0 g (95%) of the title compound. $^1H$ NMR (300 MHz, $CDCl_3$): δ 1.45 (t, J=7.0 Hz, 6H), 1.93 (br s, 1H), 4.09 (q, J=7.0 Hz, 4H), 4.62 (s, 2H), 6.57 (s, 2H). $^{13}C$ NMR (75 MHz, $CDCl_3$): δ 14.74, 64.96, 65.18, 104.30, 110.65, 140.29, 155.66. MS (ISP): 231.4 $[M+H]^+$.

Step 3: 4-Chloro-3,5-diethoxy-benzaldehyde

To a solution of (4-chloro-3,5-diethoxy-phenyl)-methanol (4.0 g, 17.34 mmol, 1.0 equiv) in THF (40 mL) was added activated $MnO_2$ (15.08 g, 173.4 mmol, 10.0 equiv) and the reaction mixture stirred for 18 h at rt. Filtration through Hyflo Super Cel and purification of the crude material by silica column chromatography using a MPLC system (CombiFlash Companion, Isco Inc.) eluting with a gradient of heptane/ethyl acetate provided 3.7 g (92%) of the title compound. $^1H$ NMR (300 MHz, $CDCl_3$): δ 1.50 (t, J=7.0 Hz, 6H), 4.19 (q, J=7.0 Hz, 4H), 7.07 (s, 2H), 9.89 (s, 1H). $^{13}C$ NMR (75 MHz, $CDCl_3$): δ 14.61, 65.22, 106.26, 118.64, 135.08, 156.22, 191.01. MS (EI): 229.4 $[M]^+$.

Intermediate B5

4-Bromo-3,5-diethoxy-benzaldehyde [CAS RN 363166-11-4]

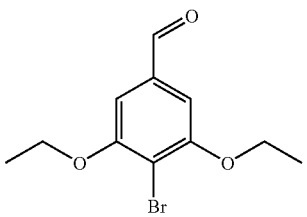

The title compound was prepared from 4-bromo-3,5-dihydroxy-benzoic acid as described in S. P. Dudek, H. D. Sikes and C. E. D. Chidsey J. Am. Chem. Soc. 2001, 123, 8033-8038.

Intermediate B6

3,5-Diethoxy-4-pyrrol-1-yl-benzaldehyde

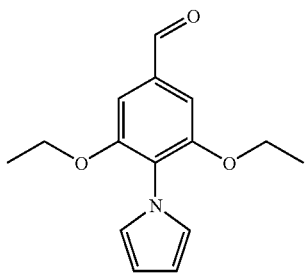

Step 1: 3,5-Diethoxy-4-pyrrol-1-yl-benzoic acid ethyl ester

To a solution of 4-amino-3,5-diethoxy-benzoic acid ethyl ester (3.0 g, 11.84 mmol, 1.0 equiv; prepared as described in I. Kompis and A. Wick *Helv. Chim. Acta* 1977, 60, 3025-3034) in heptane (10 mL) and conc. acetic acid (0.2 mL) was added 2,5-dimethoxy-tetrahydro-furan (1.88 g, 14.21 mmol, 1.2 equiv). After heating to reflux for 5 h, a Dean-Stark apparatus was attached and the reaction mixture heated for an additional time period of 5 h. Filtration of the crude reaction mixture and crystallization at 0° C. from heptane provided 2.94 g (82%) of the title compound. $^1$H NMR (300 MHz, DMSO): δ 1.15 (t, J=7.0 Hz, 6H), 1.27 (t, J=7.1 Hz, 3H), 3.98 (q, J=7.0 Hz, 4H), 4.28 (q, J=7.1 Hz, 2H), 6.07-6.08 (m, 2H), 6.73-6.74 (m, 2H), 7.22 (s, 2H). $^{13}$C NMR (75 MHz, DMSO): δ 14.11, 14.35, 61.06, 64.57, 106.87, 107.64, 122.61, 123.33, 129.29, 153.75, 165.06. MS (ISP): 303.4 [M+H]$^+$.

Step 2: 3,5-Diethoxy-4-pyrrol-1-yl-benzaldehyde

To a solution of 3,5-diethoxy-4-pyrrol-1-yl-benzoic acid ethyl ester (1.51 g, 4.98 mmol, 1.0 equiv) in toluene (5 mL) was added slowly over a time period of 15 min under slight cooling to 20° C. a solution of diisobutylaluminum hydride (8.9 mL, 12.45 mmol, 2.5 equiv; 20% solution in toluene). After 1 h, the excess of hydride was quenched by cautious addition of water (10 mL) and a 28% solution of NaOH (2 mL). The mixture was stirred for 30 min and the organic phase filtered over Hyflo Super Cel. The aqueous layer was extracted with toluene (2×50 mL), the combined organic phases washed with a sat. solution of NaCl (2×50 mL) and concentrated by evaporation under reduced pressure to afford 1.30 g (100%) of (3,5-diethoxy-4-pyrrol-1-yl-phenyl)-methanol. The crude alcohol (1.30 g, 4.98 mmol, 1.0 equiv) was dissolved in toluene (20 mL), and activated MnO$_2$ (7.79 g, 89.5 mmol, 18.0 equiv) was added. The reaction mixture was heated to reflux for 7 h, after which time the reaction mixture was filtered through Hyflo Super Cel and concentrated yielding 1.15 g (89% yield) of the title compound. $^1$H NMR (300 MHz, DMSO): δ 1.17 (t, J=7.0 Hz, 6H), 4.02 (q, J=7.0 Hz, 4H), 6.08-6.09 (m, 2H), 6.75-6.76 (m, 2H), 7.25 (s, 2H), 9.89 (s, 1H). MS (ISP): 260.1 [M+H]$^+$.

Intermediate B7

2,6-Diethoxy-4'-fluoro-biphenyl-4-carbaldehyde

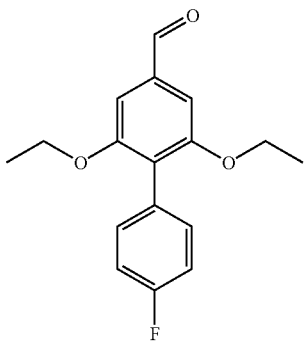

3,5-Diethoxy-4-iodo-benzaldehyde (14.05 g, 43.89 mmol, 1.0 equiv; prepared as described in WO 01/326 33 A1 (F. Hoffmann-La Roche AG); [CAS RN 338454-05-0]) was dissolved under Ar in toluene (180 mL) and water (20 mL) and treated successively with 4-fluorophenyl boronic acid (12.28 g, 87.78 mmol, 2.0 equiv), K$_3$PO$_4$ (50.12 g, 236.12 mmol, 5.38 equiv), tricyclohexylphosphine (2.80 g, 9.66 mmol, 0.22 equiv) and palladium(II) acetate (1.08 g, 4.83 mmol, 0.11 equiv). The reaction mixture was heated to 100° C. for 18 h under scrupulous exclusion of oxygen, when GC indicated the absence of starting iodo-compound. The reaction mixture was poured on crashed ice/NH$_4$Cl, extracted with ethyl acetate (2×200 mL) and the combined organic phases washed with a sat. solution of NaCl (2×100 mL) and water (2×100 mL). The organic phase was dried over Na$_2$SO$_4$, concentrated by evaporation under reduced pressure and the crude material purified by silica column chromatography eluting with a mixture of hexane/ethyl acetate (9:1). Recrystallization from hexane/ethyl acetate provided 10.44 g (83%) of the title compound as white crystals. MS (EI): 288.2 [M]$^+$.

Intermediate B8

3,5-Diethoxy-4-fluoro-benzaldehyde

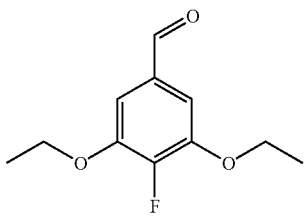

Step 1: tert-Butyl-(4-fluoro-benzyloxy)-dimethyl-silane

To a solution of (4-fluoro-phenyl)-methanol (12.16 g, 96.4 mmol, 1.0 equiv) in anhydrous DMF (50 mL) at 0° C. under Ar was added imidazole (7.22 g, 106.1 mmol, 1.1 equiv) and tert-butyl-chloro-dimethyl-silane (15.99 g, 106.1 mmol, 1.1 equiv). After the addition was completed the cooling bath was removed and the reaction stirred for 18 h at rt. The reaction mixture was poured on ice, extracted with ethyl acetate (2×100 mL) and the combined organic phases washed with a sat. solution of $Na_2CO_3$ (2×100 mL) and a sat. solution of NaCl (2×100 mL). The organic phase was dried over $Na_2SO_4$, concentrated by evaporation under reduced pressure yielding a brown oil that was purified by high vacuum destillation (bp 32-35° C. at 0.1 mbar) to give 23.0 g (99%) of the title compound. $^1$H NMR (400 MHz, $CDCl_3$): δ 0.00 (s, 6H), 0.84 (s, 9H), 4.60 (s, 2H), 6.89-6.94 (m, 2H), 7.16-7.20 (m, 2H). MS (EI): 183.1 [M-tert-Bu]$^+$.

Step 2: 5-(tert-Butyl-dimethyl-silanyloxymethyl)-2-fluoro-phenol

To a solution of tert-butyl-(4-fluoro-benzyloxy)-dimethyl-silane (5.00 g, 20.8 mmol, 1.0 equiv) in anhydrous THF (20 mL) was added at −78° C. under Ar a solution of sec-BuLi (17.6 mL, 22.8 mmol, 1.1 equiv; 1.3 M solution in hexane) within 30 min. Then a solution of trimethyl borate (2.37 mL, 2.20 g, 20.8 mmol, 1.0 equiv) in anhydrous THF (7.5 mL) was added slowly within 30 min and the cooling bath removed. A solution of conc. acetic acid (2.78 mL, 1.87 g, 31.2 mmol, 1.5 equiv) was slowly added followed by a solution of 35% hydrogen peroxide in water (2.0 mL, 2.23 g, 22.9 mmol, 1.1 equiv) and the reaction allowed to proceed at 0° C. for another 30 min. After stirring at rt for additional 4 h, the mixture was extracted with diethyl ether (2×100 mL) and the combined organic phases washed with a solution of 10% NaOH (2×100 mL) and a sat. solution of NaCl (2×100 mL). The organic phase was dried over $Na_2SO_4$, concentrated by evaporation under reduced pressure and the crude material purified with column chromatography on silica eluting with hexane/ethyl acetate (19:1) providing 4.80 g (90%) of the title compound. $^1$H NMR (400 MHz, $CDCl_3$): δ 0.00 (s, 6H), 0.84 (s, 9H), 4.56 (s, 2H), 4.97 (br s, 1H), 6.68-6.72 (m, 1H), 6.87-6.94 (m, 2H). MS (EI): 256.2 [M]$^+$.

Step 3: 2-(tert-Butyl-dimethyl-silanyloxy)-4-(tert-butyl-dimethyl-silanyloxymethyl)-1-fluoro-benzene To a solution of 5-(tert-butyl-dimethyl-silanyloxymethyl)-2-fluoro-phenol (4.60 g, 17.9 mmol, 1.0 equiv) in anhydrous DMF (20 mL) at 0° C. under Ar was added imidazole (1.34 g, 19.7 mmol, 1.1 equiv) and tert-butyl-chloro-dimethyl-silane (2.97 g, 19.7 mmol, 1.1 equiv). After the addition was completed the cooling bath was removed and the reaction stirred for 18 h at rt. The reaction mixture was poured on ice, extracted with ethyl acetate (2×100 mL) and the combined organic phases washed with a sat. solution of $Na_2CO_3$ (2×100 mL) and a sat. solution of NaCl (2×100 mL). The organic phase was dried over $Na_2SO_4$ and concentrated by evaporation under reduced pressure yielding 4.50 g (68%) of the title compound. $^1$H NMR (400 MHz, $CDCl_3$): δ 0.00 (s, 6H), 0.10 (s, 6H), 0.85 (s, 9H), 0.92 (s, 9H), 4.55 (s, 2H), 6.71-6.74 (m, 1H), 6.80-6.83 (m, 1H), 6.87-6.92 (m, 1H). MS (EI): 370.2 [M]$^+$.

Step 4: 3-(tert-Butyl-dimethyl-silanyloxy)-5-(tert-butyl-dimethyl-silanyloxymethyl)-2-fluoro-phenol To a solution of 2-(tert-butyl-dimethyl-silanyloxy)-4-(tert-butyl-dimethyl-silanyloxymethyl)-1-fluoro-benzene (23.70 g, 63.9 mmol, 1.0 equiv) in anhydrous THF (130 mL) was added at −78° C. under Ar a solution of sec-BuLi (54.5 mL, 71.6 mmol, 1.1 equiv; 1.3 M solution in hexane) within 30 min. Then a solution of trimethyl borate (7.13 mL, 6.64 g, 63.9 mmol, 1.0 equiv) in anhydrous THF (30 mL) was added slowly within 30 min and the cooling bath removed. A solution of conc. acetic acid (5.49 mL, 5.76 g, 95.9 mmol, 1.5 equiv) was slowly added followed by addition of a solution of 35% hydrogen peroxide in water (6.2 mL, 6.83 g, 70.3 mmol, 1.1 equiv) and the reaction allowed to proceed at 0° C. for another 30 min. After stirring at rt for additional 4 h, the mixture was extracted with diethyl ether (2×100 mL) and the combined organic phases washed with a solution of 10% NaOH (2×100 mL) and a sat. solution of NaCl (2×100 mL). The organic phase was dried over $Na_2SO_4$, concentrated by evaporation under reduced pressure, and the crude material was purified with column chromatography on silica eluting with hexane/ethyl acetate (19:1) providing 15.80 g (64%) of the title compound. $^1$H NMR (400 MHz, $CDCl_3$): δ 0.00 (s, 6H), 0.10 (s, 6H), 0.85 (s, 9H), 0.91 (s, 9H), 4.50 (s, 2H), 4.93 (br s, 1H), 6.37 (d, J=5.6 Hz, 1H), 6.47 (d, J=5.6 Hz, 1H). MS (EI): 329.2 [M-tert-Bu]$^+$.

Step 5: tert-Butyl-(3,5-diethoxy-4-fluoro-benzyloxy)-dimethyl-silane

To a solution of 3-(tert-butyl-dimethyl-silanyloxy)-5-(tert-butyl-dimethyl-silanyloxymethyl)-2-fluoro-phenol (5.80 g, 15.0 mmol, 1.0 equiv) in DMF (60 mL) was added $K_2CO_3$ (4.56 g, 33.0 mmol, 2.2 equiv) and ethyl bromide (2.46 mL, 3.60 g, 33.0 mmol, 2.2 equiv) and the reaction mixture stirred under Ar at 60° C. for 5 h. The $K_2CO_3$ was removed by filtration, the crude reaction mixture concentrated by evaporation under reduced pressure, the residue extracted with ethyl acetate (3×100 mL), the combined organic phases washed with water (2×100 ml) and dried over $Na_2SO_4$. The solvent was removed by evaporation under reduced pressure and the crude material purified with column chromatography on silica eluting with hexane/ethyl acetate (99:1) providing 3.10 g (63%) of the title compound. $^1$H NMR (400 MHz, $CDCl_3$): δ 0.00 (s, 6H), 0.85 (s, 9H), 1.33 (t, J=7.0 Hz, 6H), 4.00 (q, J=7.0 Hz, 4H), 4.55 (s, 2H), 6.47 (d, J=6.8 Hz, 2H). MS (ISP): 329.3 [M+H]$^+$.

Step 6: (3,5-Diethoxy-4-fluoro-phenyl)-methanol

To a solution of tert-butyl-(3,5-diethoxy-4-fluoro-benzyloxy)-dimethyl-silane (1.20 g, 3.65 mmol, 1.0 equiv) in methanol (8 mL) was added Dowex 50W-X8 (0.33 g, cation exchange resin) and the reaction mixture stirred under Ar at rt for 22 h. The resin was removed by filtration and the reaction mixture concentrated by evaporation under reduced pressure yielding the title compound in quantitative yield (0.78 g). $^1$H NMR (400 MHz, $CDCl_3$): δ 1.34 (t, J=7.0 Hz, 6H), 1.57 (t, J=5.4 Hz, 1H), 4.01 (q, J=7.0 Hz, 4H), 4.51 (d, J=5.4 Hz, 2H), 6.51 (d, J=6.8 Hz, 2H). MS (EI): 214.2 [M]$^+$.

Step 7: 3,5-Diethoxy-4-fluoro-benzaldehyde

To a solution of (3,5-diethoxy-4-fluoro-phenyl)-methanol (2.30 g, 10.7 mmol, 1.0 equiv) in 1,2-dichloroethane (50 mL) was added activated $MnO_2$ (2.89 g, 33.3 mmol, 3.1 equiv). The reaction mixture was stirred for 21 h at 50° C. and then filtered through Hyflo Super Cel providing after evaporation of the solvent under reduced pressure 1.90 g (83%) of the title compound. $^1$H NMR (400 MHz, $CDCl_3$): δ 1.38 (t, J=7.0 Hz, 6H), 4.09 (q, J=7.0 Hz, 4H), 7.04 (d, J=7.2 Hz, 2H), 9.75 (s, 1H). MS (EI): 212.1 [M]$^+$.

Intermediate B9

4-Amino-3,5-diethoxy-benzaldehyde

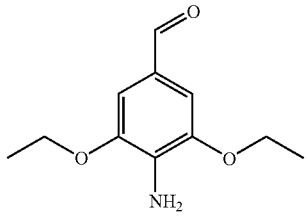

Step 1: (4-Amino-3,5-diethoxy-phenyl)-methanol

To a solution of 4-amino-3,5-diethoxy-benzoic acid ethyl ester (2.8 g, 11.05 mmol, 1.0 equiv; prepared as described in I. Kompis, A. Wick *Helv. Chim. Acta* 1977, 60, 3025-3034) in dichloromethane (50 mL) at 0° C. under Ar was slowly added diisobutylaluminum hydride (27.6 mL, 27.64 mmol, 2.5 equiv; 1.0 M solution in dichloromethane) over a time period of 15 min and the cooling bath removed on completion of addition. After stirring for 18 h, the excess of hydride was quenched by cautious addition of a sat. solution of potassium sodium tartrate (10 mL). The solidified mixture was extracted with dichloromethane (5×200 mL) and THF (2×150 mL), the combined organic phases washed with water (3×100 mL), dried over MgSO$_4$, concentrated by evaporation under reduced pressure and the crude material purified by column chromatography on silica eluting with a gradient of heptane/ethyl acetate (4:1→1:1) providing 1.10 g (47%) of the title compound. $^1$H NMR (300 MHz, CDCl$_3$): δ 1.42 (t, J=7.0 Hz, 3H), 3.82 (br s, 2H), 4.05 (q, J=7.0 Hz, 2H), 4.54 (s, 2H), 6.50 (s, 2H). $^{13}$C NMR (75 MHz, CDCl$_3$): δ 15.03, 64.21, 66.00, 104.51, 125.44, 129.89, 146.71. MS (ISP): 211.9 [M+H]$^+$.

Step 2: 4-Amino-3,5-diethoxy-benzaldehyde

To a solution of (4-amino-3,5-diethoxy-phenyl)-methanol (0.79 g, 3.74 mmol, 1.0 equiv) in DMF (20 mL) was added activated MnO$_2$ (1.63 g, 18.70 mmol, 5.0 equiv). The reaction mixture was stirred for 24 h at rt, filtered through Hyflo Super Cel, the filtrate was extracted with ethyl acetate (3×50 mL), and the combined organic phase was washed with water, dried over MgSO$_4$ and evaporated to dryness providing thereby 0.69 g (88%) of the title compound. $^1$H NMR (300 MHz, DMSO): δ 1.46 (t, J=7.0 Hz, 3H), 4.15 (q, J=7.0 Hz, 2H), 4.50 (br s, 2H), 7.04 (s, 2H), 9.70 (s, 1H). MS (ISP): 210.0 [M+H]$^+$.

Intermediate B10

3-Ethoxy-4-methyl-benzaldehyde [CAS RN 157143-20-9]

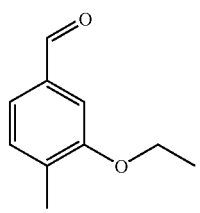

The title compound was prepared by reaction of commercially available 3-hydroxy-4-methyl-benzaldehyde with ethyl iodide in DMF using K$_2$CO$_3$ as base in analogy to the procedure described in M. J. Ashton, D. C. Cook, G. Fenton, J.-A. Karlsson, M. N. Palfreyman, D. Raeburn, A. J. Ratcliffe, J. E. Souness, S. Thurairatnam and N. Vicker *J. Med. Chem.* 1994, 37, 1696-1703.

Intermediate B11

3-Ethoxy-4-fluoro-benzaldehyde

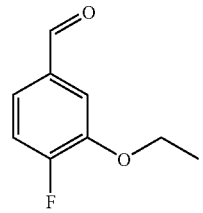

The title compound was prepared according to the procedure described for the synthesis of 4-chloro-3-ethoxy-benzaldehyde (intermediate B2) starting from 4-fluoro-3-hydroxy-benzoic acid in 73% overall yield after purification by flash column chromatography on silica eluting with hexane/ethyl acetate (10:1). $^1$H NMR (300 MHz, DMSO): δ 1.32 (t, J=7.0 Hz, 3H), 4.12 (q, J=7.0 Hz, 2H), 7.34-7.41 (m, 1H), 7.47-7.56 (m, 2H), 9.87 (s, 1H). MS (ISP): 186.1 [M+NH$_4$]$^+$.

Intermediate B12

4-Methoxy-3-propoxy-benzaldehyde [CAS RN 5922-56-5]

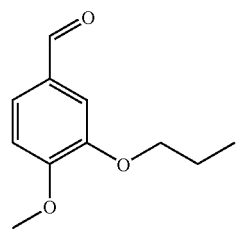

The title compound was prepared by reaction of isovanillin with propyl iodide in DMF using K$_2$CO$_3$ as base in analogy to the preparation of 3-ethoxy-4-methyl-benzaldehyde (intermediate B10).

Intermediate B13

3-(2-Fluoro-ethoxy)-4-methoxy-benzaldehyde

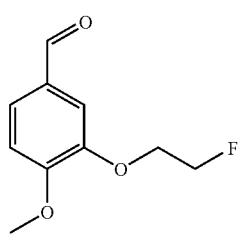

To a solution of 3-hydroxy-4-methoxy-benzaldehyde (10.0 g, 66.0 mmol, 1.0 equiv; commercially available) in anhydrous DMF (40 mL) was added $K_2CO_3$ (13.6 g, 99.0 mmol, 1.5 equiv) and 1-bromo-2-fluoro-ethane (9.2 mg, 72.0 mmol, 1.1 equiv) and the mixture stirred at rt for 48 h. The $K_2CO_3$ was removed by filtration and the organic phase concentrated under reduced pressure. To the residue was added a sat. solution of NaCl (100 mL) and the solution extracted with ethyl acetate (3×100 mL). The combined organic phases were dried over $MgSO_4$ and the product crystallized from a mixture of isopropanol/diethyl ether to yield 12.69 g (97%) of the title compound. $^1$H NMR (300 MHz, DMSO): δ 3.89 (s, 3H), 4.24-4.27 (m, 1H), 4.34-4.37 (m, 1H), 4.67-4.70 (m, 1H), 4.83-4.86 (m, 1H), 7.20 (d, J=8.4 Hz, 1H), 7.43 (d, J=1.9 Hz, 1H), 7.59 (dd, J=8.4 Hz, J=1.9 Hz, 1H), 9.84 (s, 1H). MS (ISP): 198.6 $[M+H]^+$.

Intermediate B14

3-Allyloxy-4-methoxy-benzaldehyde [CAS RN 225939-36-6]

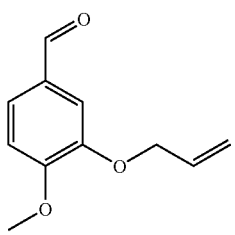

The title compound was prepared analogously to 3-ethoxy-4-methyl-benzaldehyde (intermediate B10) by reaction of 3-hydroxy-4-methoxy-benzaldehyde with allylbromide in DMF using $K_2CO_3$ as base (see also A. W. White, R. Almassy, A. H. Calvert, N. J. Curtin, R. J. Griffin, Z. Hostomsky, K. Maegley, D. R. Newell, S. Srinivasan and B. T. Golding *J. Med. Chem.* 2000, 43, 4084-4097).

Intermediate B15

3-Butoxy-4-methoxy-benzaldehyde

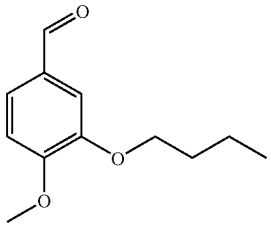

The title compound was prepared analogously to 3-ethoxy-4-methyl-benzaldehyde (intermediate B10) by reaction of 3-hydroxy-4-methoxy-benzaldehyde with 4-bromo-butane in DMF using $K_2CO_3$ as base. MS (ISP): 209.1 $[M+H]^+$.

Intermediate B16

3,5-Diethoxy-benzaldehyde [CAS RN 120355-79-5]

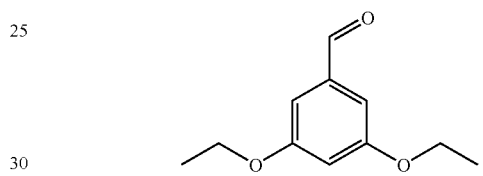

The title compound was prepared analogously to 3-ethoxy-4-methyl-benzaldehyde (intermediate B10) by reaction of 3,5-dihydroxybenzaldehyde with ethyl iodide in DMF using $K_2CO_3$ as base.

Examples 2 to 39

According to the procedure described for the synthesis of example 1/step 2 further 1,3,8-triaza-spiro[4.5]decane-2,4-dione, 2,8-diaza-spiro[4.5]decan-1-one and 1,3,8-triaza-spiro[4.5]dec-1-en-4-one derivatives have been synthesized from 1,3,8-triaza-spiro[4.5]decane 2,4-dione (intermediate A1), 2-phenyl-2,8-diaza-spiro[4.5]decan-1-one hydrochloride (intermediate A2) and 2-phenyl-1,3,8-triaza-spiro[4.5]dec-1-en-4-one hydrochloride (intermediate A3) and the respective benzaldehyde intermediate as indicated in Table 1. The results are compiled in Table 1 and comprise example 2 to example 39.

TABLE 1

| No | MW | Compound Name | Starting Materials | ISP $[M + H]^+$ |
|---|---|---|---|---|
| 2 | 337.81 | 8-(4-chloro-3-ethoxy-benzyl)-1,3,8-triaza-spiro[4.5]decane-2,4-dione | 1,3,8-triaza-spiro[4.5]decane-2,4-dione (intermediate A1) and 4-chloro-3-ethoxy-benzaldehyde (intermediate B1) | $[M + H]^+$ 338.2 |
| 3 | 361.44 | 8-(3-isobutoxy-4-methoxy-benzyl)-1,3,8-triaza-spiro[4.5]decane-2,4-dione | 1,3,8-triaza-spiro[4.5]decane-2,4-dione (intermediate A1) and 3-isobutoxy-4-methoxy-benzaldehyde (intermediate B2) | $[M + H]^+$ 362.2 |
| 4 | 375.47 | 8-(3,5-diisopropoxy-benzyl)-1,3,8-triaza-spiro[4.5]decane-2,4-dione | 1,3,8-triaza-spiro[4.5]decane-2,4-dione (intermediate A1) and 3,5-diisopropoxy-benzaldehyde (intermediate B3) | $[M + H]^+$ 376.3 |

TABLE 1-continued

| No | MW | Compound Name | Starting Materials | ISP [M + H]+ |
|---|---|---|---|---|
| 5 | 381.86 | 8-(4-chloro-3,5-diethoxy-benzyl)-1,3,8-triaza-spiro[4.5]decane-2,4-dione | 1,3,8-triaza-spiro[4.5]decane-2,4-dione (intermediate A1) and 4-chloro-3,5-diethoxy-benzaldehyde (intermediate B4) | [M + H]+ 382.3 |
| 6 | 426.32 | 8-(4-bromo-3,5-diethoxy-benzyl)-1,3,8-triaza-spiro[4.5]decane-2,4-dione | 1,3,8-triaza-spiro[4.5]decane-2,4-dione (intermediate A1) and 4-bromo-3,5-diethoxy-benzaldehyde (intermediate B5) | [M + H]+ 428.1 |
| 7 | 412.49 | 8-(3,5-diethoxy-4-pyrrol-1-yl-benzyl)-1,3,8-triaza-spiro[4.5]decane-2,4-dione | 1,3,8-triaza-spiro[4.5]decane-2,4-dione (intermediate A1) and 3,5-diethoxy-4-pyrrol-1-yl-benzaldehyde (intermediate B6) | [M + H]+ 413.3 |
| 8 | 441.50 | 8-(2,6-diethoxy-4'-fluoro-biphenyl-4-ylmethyl)-1,3,8-triaza-spiro[4.5]decane-2,4-dione | 1,3,8-triaza-spiro[4.5]decane-2,4-dione (intermediate A1) and 2,6-diethoxy-4'-fluoro-biphenyl-4-carbaldehyde (intermediate B7) | [M + H]+ 442.3 |
| 9 | 398.93 | 8-(4-chloro-3-ethoxy-benzyl)-2-phenyl-2,8-diaza-spiro[4.5]decan-1-one | 2-phenyl-2,8-diaza-spiro[4.5]decan-1-one hydrochloride (intermediate A2) and 4-chloro-3-ethoxy-benzaldehyde (intermediate B1) | [M + H]+ 399.4 |
| 10 | 426.53 | 8-(3,5-diethoxy-4-fluoro-benzyl)-2-phenyl-2,8-diaza-spiro[4.5]decan-1-one | 2-phenyl-2,8-diaza-spiro[4.5]decan-1-one hydrochloride (intermediate A2) and 3,5-diethoxy-4-fluoro-benzaldehyde (intermediate B8) | [M + H]+ 427.3 |
| 11 | 442.99 | 8-(4-chloro-3,5-diethoxy-benzyl)-2-phenyl-2,8-diaza-spiro[4.5]decan-1-one | 2-phenyl-2,8-diaza-spiro[4.5]decan-1-one hydrochloride (intermediate A2) and 4-chloro-3,5-diethoxy-benzaldehyde (intermediate B4) | [M + H]+ 443.4 |
| 12 | 423.56 | 8-(4-amino-3,5-diethoxy-benzyl)-2-phenyl-2,8-diaza-spiro[4.5]decan-1-one | 2-phenyl-2,8-diaza-spiro[4.5]decan-1-one hydrochloride (intermediate A2) and 4-amino-3,5-diethoxy-benzaldehyde (intermediate B9) | [M + H]+ 424.4 |
| 13 | 473.62 | 8-(3,5-diethoxy-4-pyrrol-1-yl-benzyl)-2-phenyl-2,8-diaza-spiro[4.5]decan-1-one | 2-phenyl-2,8-diaza-spiro[4.5]decan-1-one hydrochloride (intermediate A2) and 3,5-diethoxy-4-pyrrol-1-yl-benzaldehyde (intermediate B6) | [M + H]+ 474.3 |
| 14 | 502.63 | 8-(2,6-diethoxy-4'-fluoro-biphenyl-4-ylmethyl)-2-phenyl-2,8-diaza-spiro[4.5]decan-1-one | 2-phenyl-2,8-diaza-spiro[4.5]decan-1-one hydrochloride (intermediate A2) and 2,6-diethoxy-4'-fluoro-biphenyl-4-carbaldehyde (intermediate B7) | [M + H]+ 503.4 |
| 15 | 377.49 | 8-(3-ethoxy-4-methyl-benzyl)-2-phenyl-1,3,8-triaza-spiro[4.5]dec-1-en-4-one | 2-phenyl-1,3,8-triaza-spiro[4.5]dec-1-en-4-one hydrochloride (intermediate A3) and 3-ethoxy-4-methyl-benzaldehyde (intermediate B10) | [M + H]+ 378.3 |

TABLE 1-continued

| No | MW | Compound Name | Starting Materials | ISP [M + H]+ |
|---|---|---|---|---|
| 16 | 381.45 | 8-(3-ethoxy-4-fluoro-benzyl)-2-phenyl-1,3,8-triaza-spiro[4.5]dec-1-en-4-one | 2-phenyl-1,3,8-triaza-spiro[4.5]dec-1-en-4-one hydrochloride (intermediate A3) and 3-ethoxy-4-fluoro-benzaldehyde (intermediate B11) | [M + H]+ 382.3 |
| 17 | 397.91 | 8-(4-chloro-3-ethoxy-benzyl)-2-phenyl-1,3,8-triaza-spiro[4.5]dec-1-en-4-one | 2-phenyl-1,3,8-triaza-spiro[4.5]dec-1-en-4-one hydrochloride (intermediate A3) and 4-chloro-3-ethoxy-benzaldehyde (intermediate B1) | [M + H]+ 398.2 |
| 18 | 379.46 | 8-(3-ethoxy-4-hydroxy-benzyl)-2-phenyl-1,3,8-triaza-spiro[4.5]dec-1-en-4-one | 2-phenyl-1,3,8-triaza-spiro[4.5]dec-1-en-4-one hydrochloride (intermediate A3) and 3-ethoxy-4-hydroxy-benzaldehyde (commercially available) | [M + H]+ 380.3 |
| 19 | 393.49 | 8-(3-ethoxy-4-methoxy-benzyl)-2-phenyl-1,3,8-triaza-spiro[4.5]dec-1-en-4-one | 2-phenyl-1,3,8-triaza-spiro[4.5]dec-1-en-4-one hydrochloride (intermediate A3) and 3-ethoxy-4-methoxy-benzaldehyde (commercially available) | [M + H]+ 394.3 |
| 20 | 407.51 | 8-(3,4-diethoxy-benzyl)-2-phenyl-1,3,8-triaza-spiro[4.5]dec-1-en-4-one | 2-phenyl-1,3,8-triaza-spiro[4.5]dec-1-en-4-one hydrochloride (intermediate A3) and 3,4-diethoxy-benzaldehyde (commercially available) | [M + H]+ 408.3 |
| 21 | 419.52 | 8-(4-allyloxy-3-ethoxy-benzyl)-2-phenyl-1,3,8-triaza-spiro[4.5]dec-1-en-4-one | 2-phenyl-1,3,8-triaza-spiro[4.5]dec-1-en-4-one hydrochloride (intermediate A3) and 4-allyloxy-3-ethoxy-benzaldehyde (commercially available) | [M + H]+ 420.4 |
| 22 | 421.54 | 8-(3-ethoxy-4-isopropoxy-benzyl)-2-phenyl-1,3,8-triaza-spiro[4.5]dec-1-en-4-one | 2-phenyl-1,3,8-triaza-spiro[4.5]dec-1-en-4-one hydrochloride (intermediate A3) and 3-ethoxy-4-isopropoxy-benzaldehyde (commercially available) | [M + H]+ 422.4 |
| 23 | 435.57 | 8-(3-ethoxy-4-isobutoxy-benzyl)-2-phenyl-1,3,8-triaza-spiro[4.5]dec-1-en-4-one | 2-phenyl-1,3,8-triaza-spiro[4.5]dec-1-en-4-one hydrochloride (intermediate A3) and 3-ethoxy-4-isobutoxy-benzaldehyde (commercially available) | [M + H]+ 436.4 |
| 24 | 447.58 | 8-(4-cyclopentyloxy-3-ethoxy-benzyl)-2-phenyl-1,3,8-triaza-spiro[4.5]dec-1-en-4-one | 2-phenyl-1,3,8-triaza-spiro[4.5]dec-1-en-4-one hydrochloride (intermediate A3) and 4-cyclopentyloxy-3-ethoxy-benzaldehyde (commercially available) | [M + H]+ 448.4 |
| 25 | 469.58 | 8-(4-benzyloxy-3-ethoxy-benzyl)-2-phenyl-1,3,8-triaza-spiro[4.5]dec-1-en-4-one | 2-phenyl-1,3,8-triaza-spiro[4.5]dec-1-en-4-one hydrochloride (intermediate A3) and 4-benzyloxy-3-ethoxy-benzaldehyde (commercially available) | [M + H]+ 470.4 |
| 26 | 429.47 | 8-(4-difluoromethoxy-3-ethoxy-benzyl)-2-phenyl-1,3,8-triaza-spiro[4.5]dec-1-en-4-one | 2-phenyl-1,3,8-triaza-spiro[4.5]dec-1-en-4-one hydrochloride (intermediate A3) and 4-difluoromethoxy-3-ethoxy-benzaldehyde (commercially available) | [M + H]+ 430.3 |

TABLE 1-continued

| No | MW | Compound Name | Starting Materials | ISP [M + H]+ |
|---|---|---|---|---|
| 27 | 407.51 | 8-(4-methoxy-3-propoxy-benzyl)-2-phenyl-1,3,8-triaza-spiro[4.5]dec-1-en-4-one | 2-phenyl-1,3,8-triaza-spiro[4.5]dec-1-en-4-one hydrochloride (intermediate A3) and 4-methoxy-3-propoxy-benzaldehyde (intermediate B12) | [M + H]+ 408.3 |
| 28 | 407.51 | 8-(3-isopropoxy-4-methoxy-benzyl)-2-phenyl-1,3,8-triaza-spiro[4.5]dec-1-en-4-one | 2-phenyl-1,3,8-triaza-spiro[4.5]dec-1-en-4-one hydrochloride (intermediate A3) and 3-isopropoxy-4-methoxy-benzaldehyde (commercially available) | [M + H]+ 408.3 |
| 29 | 411.48 | 8-[3-(2-fluoro-ethoxy)-4-methoxy-benzyl]-2-phenyl-1,3,8-triaza-spiro[4.5]dec-1-en-4-one | 2-phenyl-1,3,8-triaza-spiro[4.5]dec-1-en-4-one hydrochloride (intermediate A3) and 3-(2-fluoro-ethoxy)-4-methoxy-benzaldehyde (intermediate B13) | [M + H]+ 412.3 |
| 30 | 405.50 | 8-(3-allyloxy-4-methoxy-benzyl)-2-phenyl-1,3,8-triaza-spiro[4.5]dec-1-en-4-one | 2-phenyl-1,3,8-triaza-spiro[4.5]dec-1-en-4-one hydrochloride (intermediate A3) and 3-allyloxy-4-methoxy-benzaldehyde (intermediate B14) | [M + H]+ 406.3 |
| 31 | 421.54 | 8-(3-butoxy-4-methoxy-benzyl)-2-phenyl-1,3,8-triaza-spiro[4.5]dec-1-en-4-one | 2-phenyl-1,3,8-triaza-spiro[4.5]dec-1-en-4-one hydrochloride (intermediate A3) and 3-butoxy-4-methoxy-benzaldehyde (intermediate B15) | [M + H]+ 422.4 |
| 32 | 421.54 | 8-(3-isobutoxy-4-methoxy-benzyl)-2-phenyl-1,3,8-triaza-spiro[4.5]dec-1-en-4-one | 2-phenyl-1,3,8-triaza-spiro[4.5]dec-1-en-4-one hydrochloride (intermediate A3) and 3-isobutoxy-4-methoxy-benzaldehyde (intermediate B2) | [M + H]+ 422.4 |
| 33 | 433.55 | 8-(3-cyclopentyloxy-4-methoxy-benzyl)-2-phenyl-1,3,8-triaza-spiro[4.5]dec-1-en-4-one | 2-phenyl-1,3,8-triaza-spiro[4.5]dec-1-en-4-one hydrochloride (intermediate A3) and 3-cyclopentyloxy-4-methoxy-benzaldehyde (commercially available) | [M + H]+ 434.4 |
| 34 | 407.51 | 8-(3,5-diethoxy-benzyl)-2-phenyl-1,3,8-triaza-spiro[4.5]dec-1-en-4-one | 2-phenyl-1,3,8-triaza-spiro[4.5]dec-1-en-4-one hydrochloride (intermediate A3) and 3,5-diethoxy-benzaldehyde (intermediate B16) | [M + H]+ 408.3 |
| 35 | 435.57 | 8-(3,5-diisopropoxy-benzyl)-2-phenyl-1,3,8-triaza-spiro[4.5]dec-1-en-4-one | 2-phenyl-1,3,8-triaza-spiro[4.5]dec-1-en-4-one hydrochloride (intermediate A3) and 3,5-diisopropoxy-benzaldehyde (intermediate B3) | [M + H]+ 436.4 |
| 36 | 425.50 | 8-(3,5-diethoxy-4-fluoro-benzyl)-2-phenyl-1,3,8-triaza-spiro[4.5]dec-1-en-4-one | 2-phenyl-1,3,8-triaza-spiro[4.5]dec-1-en-4-one hydrochloride (intermediate A3) and 3,5-diethoxy-4-fluoro-benzaldehyde (intermediate B8) | [M + H]+ 426.3 |
| 37 | 441.96 | 8-(4-chloro-3,5-diethoxy-benzyl)-2-phenyl-1,3,8-triaza-spiro[4.5]dec-1-en-4-one | 2-phenyl-1,3,8-triaza-spiro[4.5]dec-1-en-4-one hydrochloride (intermediate A3) and 4-chloro-3,5-diethoxy-benzaldehyde (intermediate B4) | [M + H]+ 442.3 |

TABLE 1-continued

| No | MW | Compound Name | Starting Materials | ISP [M + H]+ |
|---|---|---|---|---|
| 38 | 486.41 | 8-(4-bromo-3,5-diethoxy-benzyl)-2-phenyl-1,3,8-triaza-spiro[4.5]dec-1-en-4-one | 2-phenyl-1,3,8-triaza-spiro[4.5]dec-1-en-4-one hydrochloride (intermediate A3) and 4-bromo-3,5-diethoxy-benzaldehyde (intermediate B5) | [M + H]+ 488.2 |
| 39 | 472.59 | 8-(3,5-diethoxy-4-pyrrol-1-yl-benzyl)-2-phenyl-1,3,8-triaza-spiro[4.5]dec-1-en-4-one | 2-phenyl-1,3,8-triaza-spiro[4.5]dec-1-en-4-one hydrochloride (intermediate A3) and 3,5-diethoxy-4-pyrrol-1-yl-benzaldehyde (intermediate B6) | [M + H]+ 473.4 |

Example 40

4-(4-Chloro-benzoylamino)-1-(4-chloro-3-ethoxy-benzyl)-piperidine-4-carboxylic acid amide Step 1: 4-(4-Chloro-benzoylamino)-4-cyano-piperidine-1-carboxylic acid tert-butyl ester To a solution of 4-amino-4-cyano-piperidine-1-carboxylic acid tert-butyl ester (1.25 g, 5.55 mmol, 1.0 equiv; prepared as described in WO 03/104 236 A1 (Bristol-Myers Squibb Company); [CAS RN 331281-25-5]) in dichlormethane (30 mL) and triethylamine (1.20 mL) was added 4-chloro-benzoyl chloride (1.09 g, 6.21 mmol, 1.12 equiv; commercially available) and the reaction stirred at rt overnight. A solution of 1 M NaOH (10 mL) was added and the reaction mixture extracted with ethyl acetate. The combined organic phases were washed with water and a sat. solution of NaCl, dried over MgSO$_4$ and concentrated by evaporation under reduced pressure. The crude material was crystallized from a mixture of hexane/ethyl acetate yielding 0.71 g (44%) of the title compound as white crystals. $^1$H NMR (300 MHz, CDCl$_3$): δ 1.46 (s, 9H), 1.85 (t, J=10.2 Hz, 2H), 2.45 (br s, 2H), 3.24 (t, J=11.8 Hz, 2H), 3.99 (br d, J=13.5 Hz, 2H), 6.87 (s, 1H), 7.36 (d, J=8.4 Hz, 2H), 7.69 (d, J=8.4 Hz, 2H). MS (ISP): 364.4 [M+H]+.

Step 2: 4-Chloro-N-(4-cyano-piperidin-4-yl)-benzamide hydrochloride (Intermediate A4)

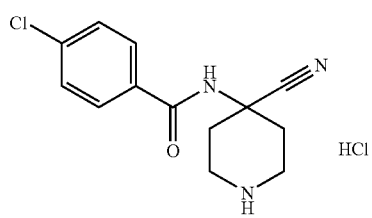

A solution of 4-(4-chloro-benzoylamino)-4-cyano-piperidine-1-carboxylic acid tert-butyl ester (0.23 g, 0.63 mmol) in 4 M HCl in dioxane (30 mL) was stirred at rt for 2 h. The solvent was removed under reduced pressure and the crude product used in the consecutive step without further purification assuming quantitative deprotection and formation of the hydrochloride salt. Note: The product is contaminated with some primary amide (partial hydrolysis of the nitrile). MS (ISP): 264.1 [M+H]+.

Step 3: 4-(4-Chloro-benzoylamino)-1-(4-chloro-3-ethoxy-benzyl)-piperidine-4-carboxylic acid amide To a solution of 4-chloro-N-(4-cyano-piperidin-4-yl)-benzamide hydrochloride (45.03 mg, 0.15 mmol, 1.0 equiv) in ethanol (1 mL), acetic acid (72.1 mg, 1.2 mmol, 8.0 equiv) and N-ethyl diisopropylamine (77.6 mg, 0.6 mmol, 4.0 equiv) was added 4-chloro-3-ethoxy-benzaldehyde (33.2 mg, 0.18 mmol, 1.2 equiv; intermediate B1) and the mixture stirred at 55° C. After 1 h, sodium cyanoborohydride (47.1 mg, 0.75 mmol, 5.0 equiv), dissolved in ethanol (0.5 mL), was added and the mixture stirred at 55° C. over night. Removal of the solvent under reduced pressure and purification by preparative HPLC on reversed phase eluting with a gradient of acetonitrile/water provided 9.7 mg (14%) of the title compound. MS (ISP): 450.2 [M+H]+.

Examples 41 and 42

According to the procedure described for the synthesis of example 40/step 3 further piperidine-4-carboxylic acid amide derivatives have been synthesized from 4-chloro-N-(4-cyano-piperidin-4-yl)-benzamide hydrochloride (intermediate A4) and the respective benzaldehyde intermediate as indicated in Table 2. The results are compiled in Table 2 and comprise example 41 and example 42.

TABLE 2

| No | MW | Compound Name | Starting Materials | ISP [M + H]+ |
|---|---|---|---|---|
| 41 | 477.96 | 4-(4-chloro-benzoylamino)-1-(3,5-diethoxy-4-fluoro-benzyl)-piperidine-4-carboxylic acid amide | 4-chloro-N-(4-cyano-piperidin-4-yl)-benzamide hydrochloride (intermediate A4) and 3,5-diethoxy-4-fluoro-benzaldehyde (intermediate B8) | [M + H]+ 478.2 |

TABLE 2-continued

| No | MW | Compound Name | Starting Materials | ISP [M + H]+ |
|---|---|---|---|---|
| 42 | 494.42 | 4-(4-chloro-benzoylamino)-1-(4-chloro-3,5-diethoxy-benzyl)-piperidine-4-carboxylic acid amide | 4-chloro-N-(4-cyano-piperidin-4-yl)-benzamide hydrochloride (intermediate A4) and 4-chloro-3,5-diethoxy-benzaldehyde (intermediate B4) | [M + H]+ 494.3 |

Example 43

N-[4-Cyano-1-(3-ethoxy-4-methyl-benzyl)-piperidin-4-yl]-5-methyl-nicotinamide

Step 1: 4-Cyano-4-[(5-methyl-pyridine-3-carbonyl)-amino]-piperidine-1-carboxylic acid tert-butyl ester To a solution of 4-amino-4-cyano-piperidine-1-carboxylic acid tert-butyl ester (0.485 g, 2.15 mmol, 1.0 equiv; prepared as described in WO 03/104 236 A1 (Bristol-Myers Squibb Company); [CAS RN 331281-25-5]) in anhydrous THF (11 mL) and N-ethyl diisopropylamine (0.44 mL) was added in the presence of (benzotriazol-1-yloxy)-tris-(dimethylamino) phosphonium hexafluorophosphate (1.047 g, 2.37 mmol, 1.1 equiv; BOP reagent) 5-methyl-nicotinic acid (0.295 g, 2.15 mmol, 1.0 equiv) and the reaction mixture stirred at 40° C. during a weekend. The reaction mixture was poured on crashed ice/NH$_4$Cl, extracted with ethyl acetate (2×200 mL) and the combined organic phases washed with a sat. solution of NaCl (2×100 mL) and water (2×100 mL). The organic phase was dried over Na$_2$SO$_4$, concentrated by evaporation under reduced pressure and the crude material purified by silica column chromatography eluting with a mixture of ethyl acetate/triethylamine (97:3) providing 0.48 g (65%) of the title compound as off-white foam. MS (ISP): 345.3 [M+H]+

Step 2: N-(4-Cyano-piperidin-4-yl)-5-methyl-nicotinamide dihydrochloride (Intermediate A5)

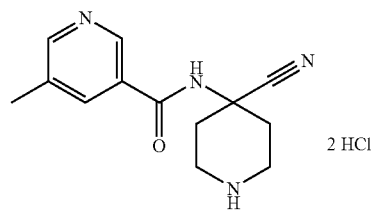

A solution of 4-cyano-4-[(5-methyl-pyridine-3-carbonyl)-amino]-piperidine-1-carboxylic acid tert-butyl ester (0.48 g, 1.39 mmol) in 4 M HCl in dioxane (7 mL) was stirred at rt for 2 h. The solvent was removed under reduced pressure and the crude product used in the consecutive step without further purification assuming quantitative deprotection and formation of the dihydrochloride salt. Note: The product is contaminated with some primary amide (partial hydrolysis of the nitrile). MS (ISP): 245.4 [M+H]+.

Step 3: N-[4-Cyano-1-(3-ethoxy-4-methyl-benzyl)-piperidin-4-yl]-5-methyl-nicotinamide To a solution of N-(4-cyano-piperidin-4-yl)-5-methyl-nicotinamide dihydrochloride (171.0 mg, 0.54 mmol, 1.0 equiv) in isopropanol (5 mL) was added 3-ethoxy-4-methyl-benzaldehyde (88.7 mg, 0.54 mmol, 1.0 equiv; intermediate B10), titanium tetra-isopropoxide (766.5 mg, 2.70 mmol, 5.0 equiv) and N-ethyl diisopropylamine (209.5 mg, 1.62 mmol, 3.0 equiv), followed by sodium cyanoborohydride (67.4 mg, 1.08 mmol, 2.0 equiv) after stirring for 1 h. The reaction mixture was allowed to react overnight and then poured directly onto a silica column eluting with ethyl acetate. The isolated crude product was purified by a second silica column eluting with dichloromethane/methanol (93:7) delivered finally 22.0 mg (24%) of the title compound as colorless oil. MS (ISP): 393.2 [M+H]+.

The 6-chloro-N-(4-cyano-piperidin-4-yl)-nicotinamide intermediate A6 was prepared as described below.

Synthesis of 6-Chloro-N-(4-cyano-piperidin-4-yl)-nicotinamide (Intermediate A6) to be used in Table 3

6-Chloro-N-(4-cyano-piperidin-4-yl)-nicotinamide dihydrochloride

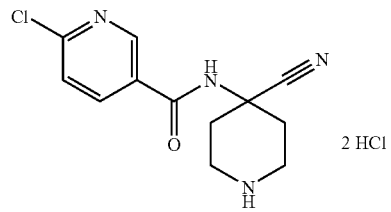

Step 1: 4-[(6-Chloro-pyridine-3-carbonyl)-amino]-4-cyano-piperidine-1-carboxylic acid tert-butyl ester To a solution of 4-amino-4-cyano-piperidine-1-carboxylic acid tert-butyl ester (0.527 g, 2.34 mmol, 1.0 equiv; prepared as described in WO 03/104 236 A1 (Bristol-Myers Squibb Company); [CAS RN 331281-25-5]) in anhydrous THF (12 mL) and N-ethyl diisopropylamine (0.48 mL) was added in the presence of (benzotriazol-1-yloxy)-tris-(dimethylamino) phosphonium hexafluorophosphate (1.138 g, 2.58 mmol, 1.1 equiv; BOP reagent) 6-chloro-nicotinic acid (0.369 g, 2.34 mmol, 1.0 equiv) and the reaction mixture stirred at rt for 12 h. The reaction mixture was poured on crashed ice/NH$_4$Cl, extracted with ethyl acetate (2×200 mL) and the combined organic phases washed with a sat. solution of NaCl (2×100 mL) and water (2×100 mL). The organic phase was dried over Na$_2$SO$_4$, concentrated by evaporation under reduced pressure and the crude material purified by silica column chromatography eluting with a mixture of ethyl acetate/triethylamine (97:3) providing 0.63 g (74%) of the title compound as off-white solid. MS (ISP): 365.1 [M+H]+

Step 2: 6-Chloro-N-(4-cyano-piperidin-4-yl)-nicotinamide dihydrochloride

A solution of 4-[(6-chloro-pyridine-3-carbonyl)-amino]-4-cyano-piperidine-1-carboxylic acid tert-butyl ester (0.30 g, 0.82 mmol) in 4 M HCl in dioxane (4 mL) was stirred at rt for 1 h. The solvent was removed under reduced pressure and the crude product used in the consecutive step without further purification assuming quantitative deprotection and formation of the dihydrochloride salt. Note: The product is contaminated with some primary amide (partial hydrolysis of the nitrile). MS (ISP): 265.3 [M+H]$^+$.

Examples 44 to 46

According to the procedure described for the synthesis of example 43/step 3 further 5-methyl-nicotinamide derivatives have been synthesized from N-(4-cyano-piperidin-4-yl)-5-methyl-nicotinamide dihydrochloride (intermediate A5) and 6-chloro-N-(4-cyano-piperidin-4-yl)-nicotinamide dihydrochloride (intermediate A6) and the respective benzaldehyde intermediate as indicated in Table 3. The results are compiled in Table 3 and comprise example 44 to example 46.

TABLE 3

| No | MW | Compound Name | Starting Materials | ISP [M + H]$^+$ |
|---|---|---|---|---|
| 44 | 440.52 | N-[4-cyano-1-(3,5-diethoxy-4-fluoro-benzyl)-piperidin-4-yl]-5-methyl-nicotinamide | N-(4-cyano-piperidin-4-yl)-5-methyl-nicotinamide dihydrochloride (Intermediate A5) and 3,5-diethoxy-4-fluoro-benzaldehyde (intermediate B8) | [M + H]$^+$ 441.3 |
| 45 | 477.39 | 6-chloro-N-[1-(4-chloro-3,5-diethoxy-benzyl)-4-cyano-piperidin-4-yl]-nicotinamide | 6-chloro-N-(4-cyano-piperidin-4-yl)-nicotinamide dihydrochloride (intermediate A6) and 4-chloro-3,5-diethoxy-benzaldehyde (intermediate B4) | [M + H]$^+$ 477.0 |
| 46 | 537.03 | 6-chloro-N-[4-cyano-1-(2,6-diethoxy-4'-fluoro-biphenyl-4-ylmethyl)-piperidin-4-yl]-nicotinamide | 6-chloro-N-(4-cyano-piperidin-4-yl)-nicotinamide dihydrochloride (intermediate A6) and 2,6-diethoxy-4'-fluoro-biphenyl-4-carbaldehyde (intermediate B7) | [M + H]$^+$ 537.4 |

Example A

Film coated tablets containing the following ingredients can be manufactured in a conventional manner:

| Ingredients | Per tablet | |
|---|---|---|
| Kernel: | | |
| Compound of formula I | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titanium dioxide | 0.8 mg | 1.6 mg |

The active ingredient is sieved and mixed with microcrystalline cellulose and the mixture is granulated with a solution of polyvinylpyrrolidone in water. The granulate is mixed with sodium starch glycolate and magnesium stearate and compressed to yield kernels of 120 mg or 350 mg, respectively. The kernels are lacquered with an aqueous solution/suspension of the above mentioned film coat.

Example B

Capsules containing the following ingredients can be manufactured in a conventional manner:

| Ingredients | Per capsule |
|---|---|
| Compound of formula I | 25.0 mg |
| Lactose | 150.0 mg |
| Maize starch | 20.0 mg |
| Talc | 5.0 mg |

The components are sieved and mixed and filled into capsules of size 2.

Example C

Injection solutions can have the following composition:

| | |
|---|---|
| Compound of formula I | 3.0 mg |
| Gelatine | 150.0 mg |
| Phenol | 4.7 mg |
| Sodium carbonate | to obtain a final pH of 7 |
| Water for injection solutions | ad 1.0 ml |

Example D

Soft gelatin capsules containing the following ingredients can be manufactured in a conventional manner:

| Capsule contents | |
|---|---|
| Compound of formula I | 5.0 mg |
| Yellow wax | 8.0 mg |
| Hydrogenated Soya bean oil | 8.0 mg |
| Partially hydrogenated plant oils | 34.0 mg |
| Soya bean oil | 110.0 mg |
| Weight of capsule contents | 165.0 mg |
| Gelatin capsule | |
| Gelatin | 75.0 mg |
| Glycerol 85% | 32.0 mg |
| Karion 83 | 8.0 mg (dry matter) |
| Titanium dioxide | 0.4 mg |
| Iron oxide yellow | 1.1 mg |

The active ingredient is dissolved in a warm melting of the other ingredients and the mixture is filled into soft gelatin capsules of appropriate size. The filled soft gelatin capsules are treated according to the usual procedures.

Example E

Sachets containing the following ingredients can be manufactured in a conventional manner:

| | |
|---|---|
| Compound of formula I | 50.0 mg |
| Lactose, fine powder | 1015.0 mg |
| Microcrystalline cellulose (AVICEL PH 102) | 1400.0 mg |
| Sodium carboxymethyl cellulose | 14.0 mg |
| Polyvinylpyrrolidone K 30 | 10.0 mg |
| Magnesium stearate | 10.0 mg |
| Flavoring additives | 1.0 mg |

The active ingredient is mixed with lactose, microcrystalline cellulose and sodium carboxymethyl cellulose and granulated with a mixture of polyvinylpyrrolidone in water. The granulate is mixed with magnesium stearate and the flavouring additives and filled into sachets.

It is to be understood that the invention is not limited to the particular embodiments of the invention described above, as variations of the particular embodiments may be made and still fall within the scope of the appended claims.

What is claimed is:

1. A compound, of formula I:

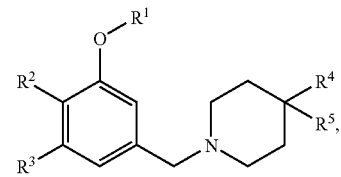

wherein
R' is selected from the group consisting of $C_{2-7}$-alkyl, $C_{2-7}$-alkenyl, $C_{3-7}$-alkinyl, $C_{3-7}$-cycloalkyl, halogen-$C_{1-7}$-alkyl, $C_{1-7}$-alkoxy-$C_{1-7}$-alkyl and benzyl;

$R^2$ is selected from the group consisting of hydrogen, $C_{1-7}$-alkyl,
hydrogen, $C_{1-7}$-alkyxy, $C_{2-7}$-alkenyloxy,
hydroxy-$C_{1-7}$-alkoxy, $C_{1-7}$-alkoxy-$C_{1-7}$-alkoxy,
—O-benzyl, —O—$C_{3-7}$-cycloalkyl,
halogen, halogen-$C_{1-7}$-alkyl, halogen-$C_{1-7}$-alkoxy,
amino, pyrrolyl, imidazolyl,
—C(O)OR$^6$, wherein R$^6$ is $C_{1-7}$-alkyl, and
unsubstituted phenyl or phenyl substituted by one to three groups independently selected from $C_{1-7}$-alkyl, halogen and $C_{1-7}$-alkoxy;

$R^3$ is hydrogen or $C_{1-7}$-alkoxy;
$R^4$ and $R^5$ are bonded to each other to form a ring together with the carbon atom to which they are attached, and $R^4$ and $R^5$ together are:
—NH—C(O)—NH—C(O)—,
and pharmaceutically acceptable salts thereof.

2. The compound according to claim 1, wherein A is O.

3. The compound according to claim 1, wherein $R^1$ is selected from the group consisting of $C_{2-7}$-alkyl, $C_{2-7}$-alkenyl, $C_{3-7}$-cycloalkyl and halogen-$C_{1-7}$-alkyl.

4. The compound according to claim 1, wherein $R^1$ is selected from the group consisting of ethyl, propyl, isopropyl, allyl, 2-fluoroethyl, isobutyl and cyclopentyl.

5. The compound according to claim 1, wherein $R^2$ is selected from the group consisting of
hydrogen, $C_{1-7}$-alkyl,
$C_{1-7}$-alkoxy, $C_{2-7}$-alkenyloxy,
—O-benzyl, —O—$C_{3-7}$-cycloalkyl,
halogen, halogen-$C_{1-7}$-alkyl, halogen-$C_{1-7}$-alkoxy,
amino, pyrrolyl, imidazolyl, and
unsubstituted phenyl or phenyl substituted by one to three groups independently selected from $C_{1-7}$-alkyl, halogen and $C_{1-7}$-alkoxy.

6. The compound according to claim 1, wherein $R^2$ is selected from the group consisting of hydrogen, $C_{1-7}$-alkoxy, $C_{2-7}$-alkenyloxy, halogen, halogen-$C_{1-7}$-alkoxy, pyrrolyl and phenyl substituted by halogen.

7. The compound according to claim 1, wherein $R^2$ is halogen.

8. The compound according to claim 1, wherein $R^3$ is $C_{1-7}$-alkoxy.

9. The compound according to claim 1, wherein $R^4$ and $R^5$ are bonded to each other to form a ring together with the carbon atom to which they are attached, and $R^4$ and $R^5$ together are —NH—C(O)—NH—C(O)—.

10. The compound according to claim 1, wherein said compound is: 8-(3-ethoxy-4-methyl-benzyl)-1,3,8-triza-spiro[4.5]decane-2,4-dione, 8-(4-chloro-3-ethoxy-benzyl)-1,3,8-triza-spiro[4.5]decane-2,4-dione, 8-(3-isobutoxy-4- methoxy-benzyl)-1,3,8-triza-spiro[4.5]decane-2,4-dione, 8-(3,5-diisopropoxy-benzyl)-1,3,8-triza-spiro[4.5]decane-2,4-dione, 8-(4-chloro-3,5-diethoxy-benzyl)-1,3,8-triza-spiro[4.5]decane-2,4-dione, 8-(4-bromo-3,5-diethoxy-benzyl)-1,3,8-triza-spiro[4.5]decane-2,4-dione, 8-(3,5-diethoxy-4-pyrrol-1-benzyl)-1,3,8-triza-spiro[4.5]decane-2,4-dione, 8-(2,6-diethoxy-4'-fluoro-biphenyl-4-ylmethyl)-1,3,8-triza-spiro[4.5]decane-2,4-dione.

11. The compound according to claim 1, wherein said compound is: 8-(4-chloro-3,5-diethoxy-benzyl)-1,3,8-triza-spiro[4.5]decane-2,4-dione, 8-(4-bromo-3,5-diethoxy-benzyl)-1,3,8-triza-spiro[4.5]decane-2,4-dione, 8-(3,5-diethoxy-4-pyrrol-1-yl-benzyl)-1,3,8-triza-spiro[4.5]decane-2,4-dione, 8-(2,6-diethoxy-4'-fluoro-biphenyl-4-ylmethyl)-1,3,8-triza-spiro[4.5]decane-2,4-dione.

12. A process for the manufacture of a compound according to claim 1, comprising the steps of:
a) reacting a piperidine of the formula

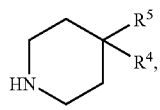

wherein $R^4$ and $R^5$ are as defined in claim 1,
with an aldehyde of the formula

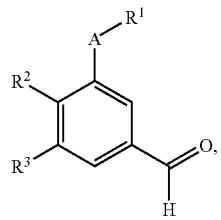

wherein A and $R^1$ to $R^3$ are as defined in claim 1,
by employing a reducing agent to obtain a compound of the formula

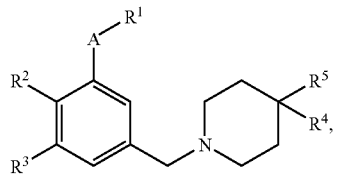

and, if desired, converting the compound of formula I into a pharmaceutically acceptable salt; or, alternatively,
b) alkylating a piperidine of the formula

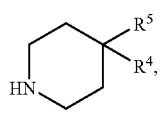

wherein $R^4$ and $R^5$ are as defined in claim 1, with a compound of the formula

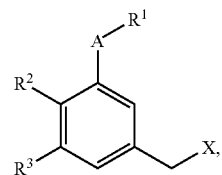

wherein A and $R^1$ to $R^3$ are as defined in claim 1 and X is a leaving group,
under basic conditions to obtain a compound of formula

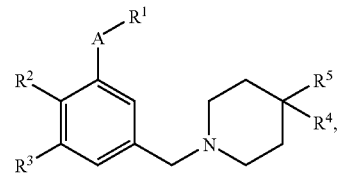

and, if desired, converting the compound of formula I into a pharmaceutically acceptable salt; or, alternatively,
c) reacting a compound of the general formula

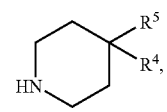

wherein $R^4$ and $R^5$ are as defined in claim 1,
with a compound of the formula

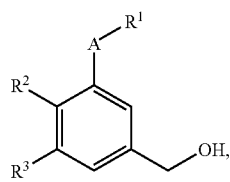

wherein A and $R^1$ to $R^3$ are as defined in claim 1, in the presence of a trialkylphosphine and a diazo-compound to obtain a compound of the formula

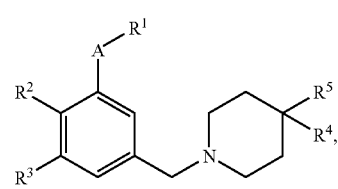

and, if desired, converting the compound of formula I into a pharmaceutically acceptable salt.

13. A pharmaceutical composition, comprising a therapeutically effective amount of a compound according to claim 1 or a pharmaceutically acceptable salt thereof and a pharmaceutically acceptable carrier and/or adjuvent.

* * * * *

UNITED STATES PATENT AND TRADEMARK OFFICE
CERTIFICATE OF CORRECTION

PATENT NO. : 8,026,365 B2  
APPLICATION NO. : 12/111230  
DATED : September 27, 2011  
INVENTOR(S) : Andreas D. Christ et al.

Page 1 of 1

It is certified that error appears in the above-identified patent and that said Letters Patent is hereby corrected as shown below:

Title Page;

In Column 1, (75) please delete "Andreas Christ, Arleshiem" and

Insert: -- Andreas D. Christ, Arlesheim --.

In Column 1, (75) please delete "Rainer Martin" and insert: -- Rainer E. Martin --.

In Column 1, (73) please delete "Hoffman" and insert -- Hoffmann --.

Signed and Sealed this  
Seventeenth Day of April, 2012

David J. Kappos  
*Director of the United States Patent and Trademark Office*